United States Patent [19]

Middeldorp et al.

[11] Patent Number: 6,008,327
[45] Date of Patent: Dec. 28, 1999

[54] PEPTIDES AND NUCLEIC ACID SEQUENCES RELATED TO THE EPSTEIN BARR VIRUS

[75] Inventors: Jaap M. Middeldorp; Wouterus M. J. van Grunsven, both of Oss, Netherlands

[73] Assignee: Akzo Nobel, N.V., Arnhem, Netherlands

[21] Appl. No.: 08/415,838

[22] Filed: Apr. 3, 1995

Related U.S. Application Data

[62] Division of application No. 08/031,148, Mar. 12, 1993, Pat. No. 5,424,398.

[30] Foreign Application Priority Data

Mar. 13, 1992 [EP] European Pat. Off. ............. 92200721

[51] Int. Cl.$^6$ ............................. C07K 16/00; C12P 21/08
[52] U.S. Cl. ...................................... 530/388.3; 530/388.1; 436/399; 436/325; 436/326; 424/230.1
[58] Field of Search ................................ 530/350, 387.1, 530/387.2, 388.1, 388.3, 391.1, 389.1; 436/513, 532, 548, 325, 326, 339; 435/513, 532, 548; 424/130.1, 131.1, 135, 136.1, 139.1, 141.1, 147.1, 156.1, 159.1, 204.1, 230.1

[56] References Cited

U.S. PATENT DOCUMENTS

| | | | |
|---|---|---|---|
| 4,699,880 | 10/1987 | Goldstein | 435/172.2 |
| 4,731,237 | 3/1988 | Reagan et al. | 428/86 |

FOREIGN PATENT DOCUMENTS

| | | |
|---|---|---|
| 0316170 | 5/1989 | European Pat. Off. . |
| 3102091 | 2/1991 | WIPO . |
| 9108224 | 6/1991 | WIPO . |
| 9109127 | 6/1991 | WIPO . |

OTHER PUBLICATIONS

R. Baer et al., *Nature*, 310;207–211, Jul. 19, 1984, London, GB.
G. Brayliss et al., *J. Gen. Virol.*, 56:105–118, 1981, London, GB.
van Grunsven et al., *J. of Virology*, 67(7):3908–3916, Jul. 1993.
Roitt. et al., immunology, 3$^{rd}$ Ed., Mosby–Yearbook Europe Limited, 1993, 4.1–4.20. Boston.
Middeldorp, et al., J. Virol. methods, 21:133–146 (1988).
Johnstone & Thorpe, Immunochemistry in practice, 2nd Ed., Blackwell Scientific Publications, boston, 1987, 30–46.
Edson et al., J. Immuno., vol. 130, No.2 : 919–924.
Wielaard, et al., J. Virol. Methods, 21:105–115 (1988).
Thorley–Lawson, David, Biochimica Biophysica Acta, 948:263–286,1988.

*Primary Examiner*—Marian C. Knode
*Assistant Examiner*—Jay Williams
*Attorney, Agent, or Firm*—Mary E. Gormley

[57] ABSTRACT

The present invention relates to peptides immunochemically reactive with antibodies to the Epstein-Barr virus (EBV), comprising at least part of the VCA-p18 or VCA-p40 protein, encoded within the EBV open reading frames BFRF3 and BdRF1 respectively, or a functional variant thereof. The invention further relates to nucleic acid sequences encoding these peptides, monoclonal antibodies against these peptides, cell lines capable of producing monoclonal antibodies and anti-idiotype antibodies. The invention also relates to recombinant vector molecules comprising a nucleic acid sequence according to the invention and host cells transformed or transfected with these vector molecules. The invention is further concerned with immunological reagents and methods for the detection of EBV or anti-EBV antibodies and a method for the amplification and detection of Epstein Barr viral nucleic acid.

4 Claims, 11 Drawing Sheets

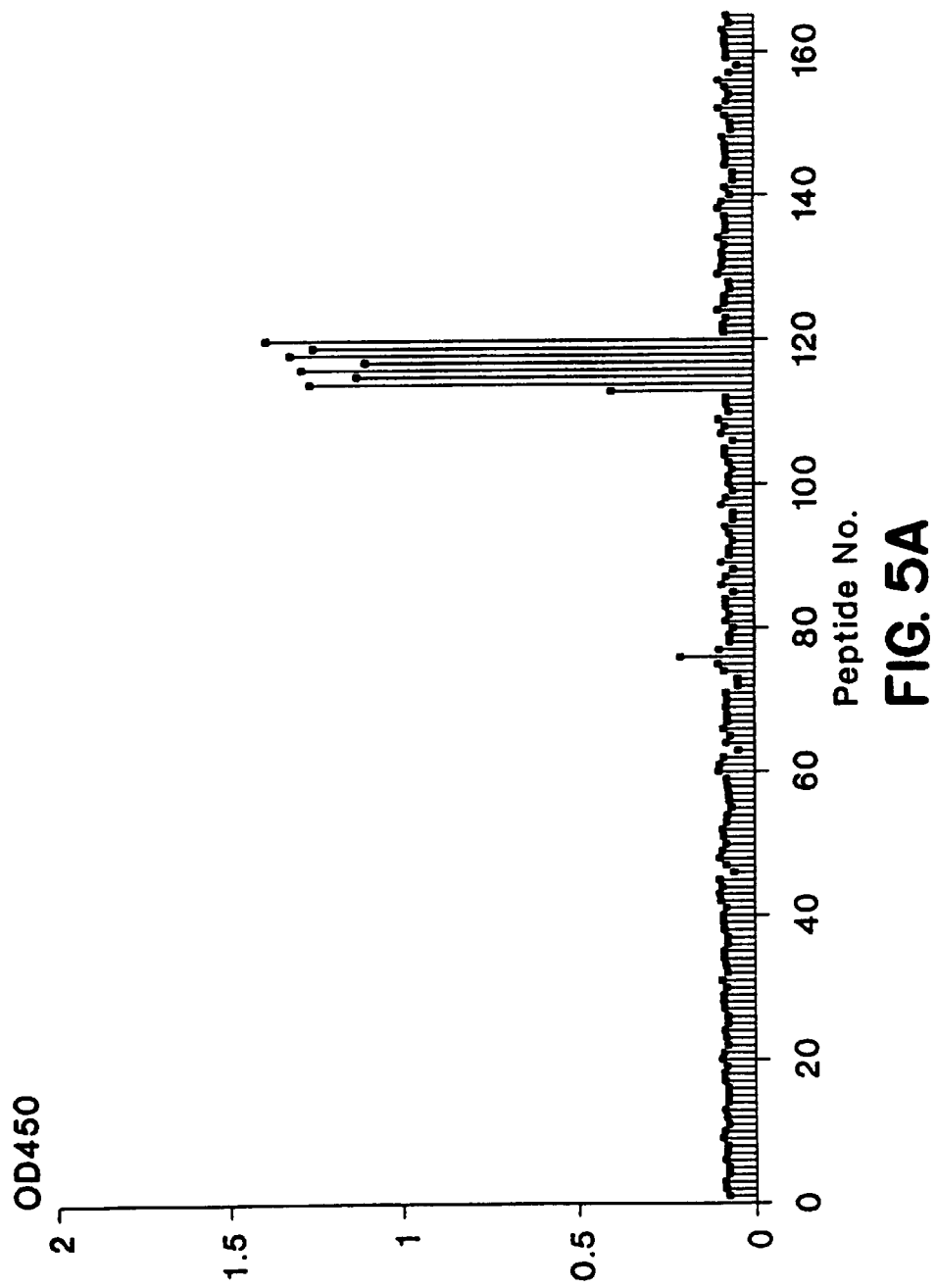

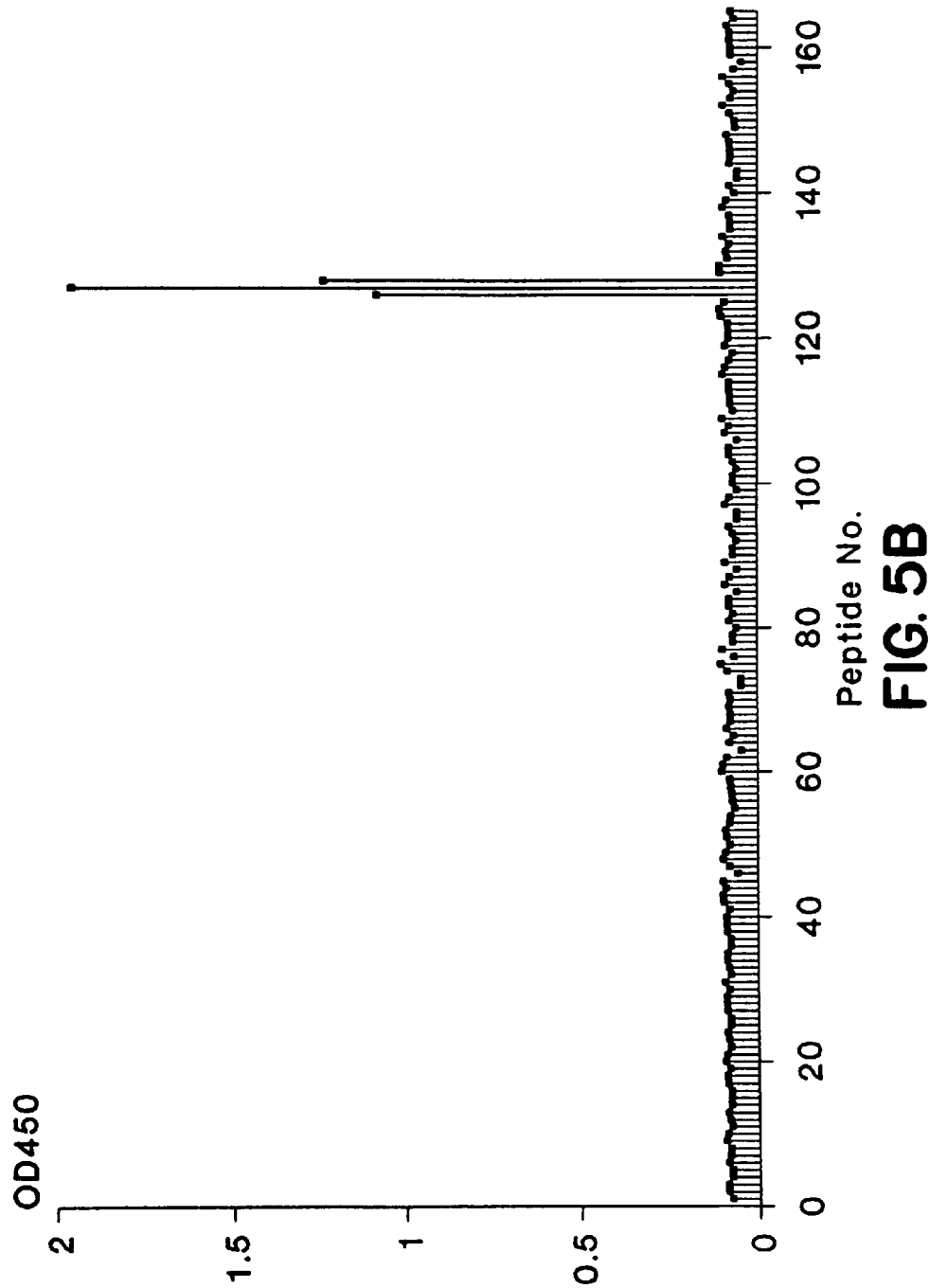

PEPSCAN: MoAb. EBV.OT41A VCA-p40 (BdRF1)

FIG. 6

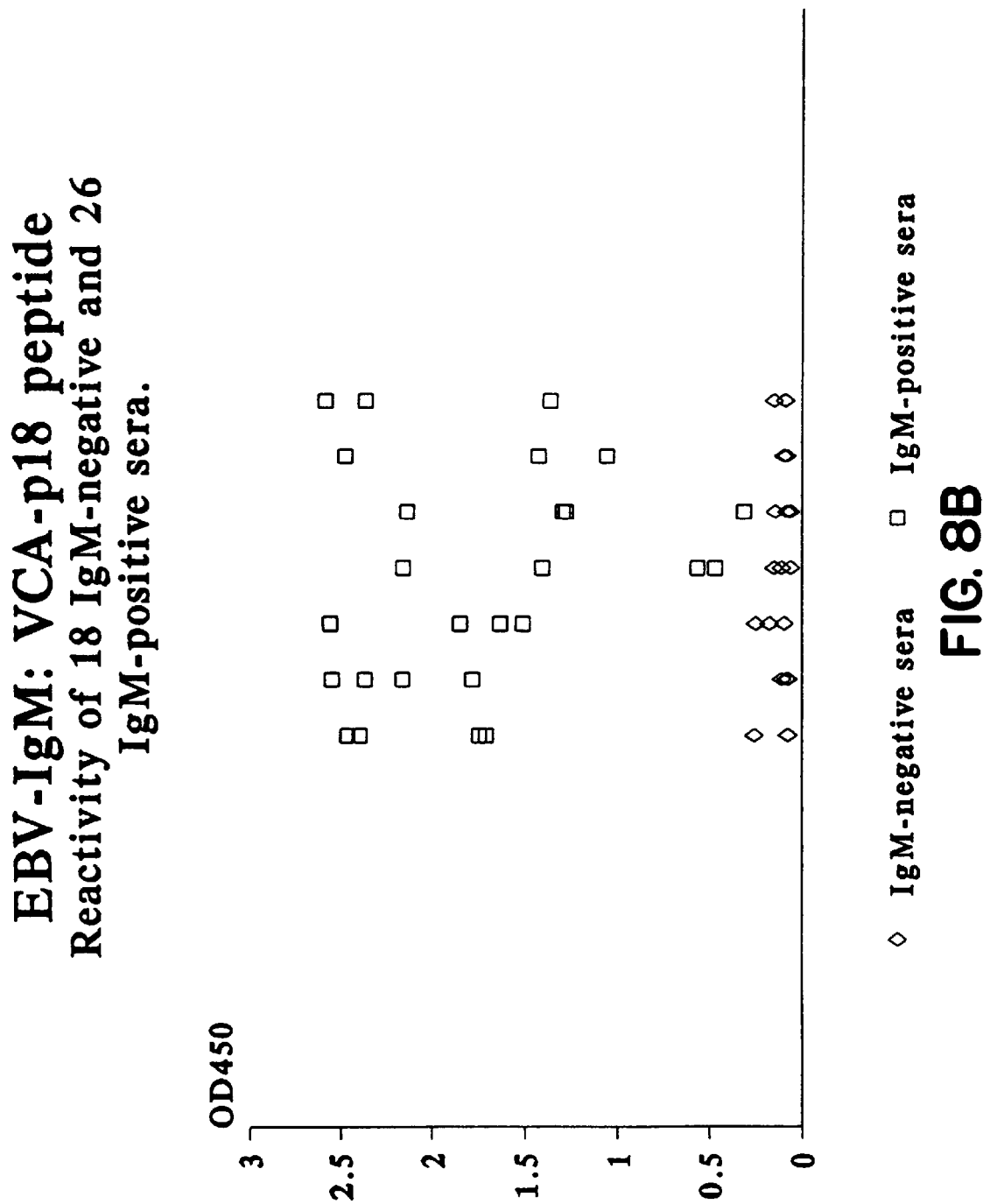

PEPTIDES AND NUCLEIC ACID SEQUENCES RELATED TO THE EPSTEIN BARR VIRUS

This is a division of application Ser. No. 08/031,148 filed Mar. 12, 1993 now U.S. Pat. No. 5,424,398.

FIELD OF THE INVENTION

The present invention relates to peptides immunochemically reactive with antibodies to the Epstein-Barr virus (EBV), nucleic acid sequences encoding these peptides, monoclonal antibodies against these peptides, cell lines capable of producing monoclonal antibodies and anti-idiotype antibodies. The invention also relates to recombinant vector molecules comprising a nucleic acid sequence according to the invention and host cells transformed with these vector molecules. The invention is further concerned with immunological reagents and methods for the detection of EBV or anti-EBV antibodies and a method for the amplification and detection of Epstein Barr viral nucleic acid.

BACKGROUND OF THE INVENTION

EBV is a ubiquitous human herpes virus that was first discovered in association with the African (endemic or e) form of Burkitt's lymphoma (BL). Subsequently the virus was also found associated with nasopharyngeal carcinoma (NPC) and was shown to be the causative agent of infectious mononucleosis (IM). Infection usually occurs during early childhood, generally resulting in a subclinical manifestation, occasionally with mild symptoms. Infection during adolescence or adulthood, however, can give rise to IM characterized by the presence of atypical lymphocytes in the periphery. The bulk of these lymphocytes are T lymphocytes; however, included in their number are a small population of B lymphocytes infected by EBV. The infection of B lymphocytes may also be accomplished in vitro. Such cells become transformed and proliferate indefinitely in culture and have been referred to as "immortalized", "latently infected" or "growth transformed ". As far as is known, all individuals who become infected with EBV remain latently infected for life. This is reflected by the lifelong continuous presence of small numbers of EBV genome-positive transformed B-cells among the circulating peripheral blood lymphocytes and the continuous but periodic shedding of virus in the oropharynx.

In the vast majority of cases EBV infection results in a lymphoproliferative disease that may be temporarily debilitating, but is always benign and self-limiting. In certain immunosuppressed individuals, however, the result can be full-blown malignancy. This occurs in individuals who are immunosuppressed intentionally, particularly children receiving organ transplants who are treated with cyclosporine A, or opportunistically, as in the case with individuals infected with HIV, or genetically, as in the case of affected males carrying the XLP (x-linked proliferative syndrome) gene. In these cases the resulting malignancies derive from the polyclonal proliferation of EBV-infected B-cells. In addition, in such patients uncontrolled epithelial replication of the virus is detectable in lesions of oral hairy leukoplakia. Thus, the immune response plays a central role in the control of EBV infection.

As mentioned above, EBV is a member of the herpesviruses. It possesses the following structural properties:
The EBV genome consists of a linear double stranded DNA molecule (173,000 base pairs).

The virion consists of a core (proteins and DNA), surrounded by an icosahedral capsid, and a membrane envelope enclosing the capsid. The icosahedral capsid is built up of hexameric and pentameric capsomeres. The membrane envelope consists of a protein/lipid brayer membrane with spikes on its outer surface. The space between the capsid shell and the envelope is filled with amorphous protein, called the tegument.

Like all herpesviruses, EBV is capable of establishing a latent life-long infection in its host subsequent to primary infection. This latency represents a perfect balance between EBV and its human host, controlled by the host's immune system.

To date, most biochemical and biological studies have been performed on three prototype strains of EBV, being B95-8 (transforming virus produced in a marmoset cell line), P3HR1 (non-transforming virus produced by a Burkitt's lymphoma tumor cell line) and Raji (latent virus in a Burkitt's lymphoma tumor cell line).

During the last few years the entire DNA sequence of the prototype virus strain, B95-8, has been determined. Analysis of this sequence has resulted in the identification of more than 80 open reading frames (Baer et al., 1984, Nature 310, p. 207–211).

The biology of EBV poses a special problem to investigators because its biological characteristics (latent infection) do not lend itself to the classic virus analysis. Furthermore, its cell and host range are effectively limited to human (and those of a few higher primates) B-lymphocytes and epithelial cells which are generally not amenable to culture in vitro. In addition, the absence of a fully permissive cell type, one in which the virus lytically replicates, has severely limited the ability to produce large amounts of the virus.

DNA molecules of B95-8, P3HR1 and Raji isolates have been the prototypes for detailed restriction endonuclease mapping, for cloning into *Escherichia coli* (*E.coli*) plasmids and in bacteriophage lambda, and for nucleotide sequencing.

The EBV genome consists of a single double-stranded DNA molecule built up of unique and tandemly repeated DNA elements. Each end of the DNA molecule contains multiple terminal sequences which permit covalently linking and circularization of the genome. In virus particles the EBV genome is only detectable in a linear form. On the contrary, it exists as a circular episome inside the nucleus of latently infected cells.

The internal repeat sequences, IR1 to IR4, separate the EBV genome into 5 unique regions. The U2 and U3 regions vary extensively among different EBV isolates, the former being almost entirely deleted in the P3HR-1 strain of EBV.

The nomenclature for EBV reading frames is based on their position in the virus genome. The names begin with the initials of the BamH1 or EcoR1 restriction fragment where expression begins. The third letter in the name is L or R, depending or whether the expression is leftward or rightward on the standard map. (So BLLF2 is the second leftward reading frame starting in BamH1 restriction fragment L.)

The serological classification of virus antigens in the productive cycle of EBV is based on different fluorescence techniques. Antigens specifically detected by means of the anticomplement immunofluorescence technique in the nucleus of fixed, latently infected B-cells (e.g. Raji-cells) are classified as Epstein-Barr nuclear antigens (EBNA). Upon activation of viral gene expression by chemical or viral factors, a class of early antigens (EA) is detected whose synthesis is not blocked by inhibition of viral DNA synthesis. Dependent on the type of fixative used (methanol or acetone) two distinct sets of EA are detectable, $EA_R$ and EA$_D$. EA is detectable by indirect immunofluorescence in the cytoplasm and nucleus of induced cells. Following onset of viral DNA synthesis (and depending upon it) virus structural proteins (VCA) are synthesized which are detectable by indirect immunofluorescence in the cytoplasm and nucleus of virus producer cells (e.g. P$_3$HR$_1$ cells). On the surface of viable infected cells, induced for virus production, a set of antigens (MA) is detectable by indirect immunofluorescence. These antigens can also be found on the viral envelope and are important targets for virus neutralization. Detection of EBV-specific antibodies in human sera can routinely be performed by serological techniques as described by Menke and Henle (Human Pathology, 5, 551–565, 1974).

Based upon biochemical and immunofluorescence data it is possible to distinguish five different classes of antigen molecules. The different viral polypeptides are designated by their molecular weight, and no common nomenclature has been established except for the virus envelope proteins.

The five different groups of antigens are:
A. The group of antigens which are expressed during a state of latency (EBNAs and LMPs).
B. The group of antigens which are responsible for genome activation and initial induction of viral replication (IEA).
C. The group of antigens which are induced by IEA gene products and which are required for replication of viral DNA; these antigens are mostly viral enzymes (EA).
D. The group of antigens which are structural components of the viral particle and are expressed late in the viral replication cycle (VCA), after initiation of viral DNA synthesis.
E. The group of antigens which are expressed in the cell membrane of the infected cell (MA).

The viral capsid antigens (VCA) of EBV.

For this antigen complex it is of concern that comparison of EBV specific proteins identified in different studies is difficult because of variations in polyacrylamide gel systems, cell lines and chemical inducers used, and the sera employed. Dolyniuk et al. (1 979) described a total of 33 proteins associated with purified virions. Differential solubilization with detergents suggest that the nucleocapsid is composed of at least seven proteins. An important component of the VCA complex is the major capsid protein (MCP). The EBV-MCP is encoded within the BcLF1 reading frame of the viral genome (Bear et al., 1984) and expressed as a 153–160 kDa non-glycosylated protein in EBV-producer cell lines, with a pI of 7.5 to 9.0. This protein is synthesized in the cytoplasm in a soluble form and then transported to the nucleus, where it condenses into capsids and is no longer solubilized by detergents. Another major VCA component has a molecular weight of 125 kDa and is glycosylated. This protein is encoded within the BALF4 reading frame of the viral genome. Although this glycoprotein was classified originally as a VCA component, recent findings indicate that it might in fact be associated with cytoplasmic and nuclear membrane structures.

Experiments described previously (J. M. Middeldorp and P. Herbrink, J.Virol.Meth., 21, 133–146, 1988) were aimed at the identification and characterization of diagnostically relevant EBV marker proteins in relation to different EBV diseases. This was done by using immunoblot strips containing antigens prepared from the virus producer cell line HH514-C16 (a superinducible derivative of P3HR1), induced for the expression of VCA/EA or EA, and from the EBV negative cell lines Ramos and Bjab. Cell lines which carry the EBV genome in a (fully) latent state, X50-7 and JC-5, can be used to study EBNA/LMP specifically.

Patterns of EBV antibody responses were studied in sera of healthy seropositive blood donors, in sera of IM patients and chronic IM patients or patients with EBV-associated tumors like nasopharyngeal carcinoma. Polyclonal and monoclonal antibodies reactive with defined EBV genome products can be used to characterize some of the protein bands detected in this experimental system. These studies however only described proteins or polypeptides with a certain molecular weight. No information was available as to the coding sequence on the EBV genome for these proteins. Nor was it known whether immunoreactive bands on immunoblots were due to reactivity with single or multiple proteins of the same molecular weight.

With immunoblot techniques it is possible to detect an EBV antigen with a molecular weight of 18 kDa. This protein is not expressed when phosphonoacetic acid (PAA) is used to block viral DNA synthesis and is detected by all sera which contain anti-VCA antibodies, which indicates that it is a VCA-related component. Another VCA component is a protein with a molecular weight of 40 kDa. Many of the viral capsid antigens are associated with the nuclear pellet.

At present EBV specific serodiagnosis is accomplished by rather subjective immunofluorescence tests. Progress to more simple and uniform diagnosis (e.g. ELISA) is hampered because bulk production and purification of viral antigens are not possible using standard virus producing cell lines. The only way to achieve this would be to use alternatively prepared EBV antigen(s). These EBV antigens could be prepared with either genetic engineering techniques or synthetic peptide techniques.

SUMMARY OF THE INVENTION

For the development of a specific and sensitive method to enable a reliable diagnosis to be made in various phases of infection with EBV it is of great importance to identify immunodominant viral proteins and epitopes thereof.

The present invention provides peptides comprising at least part of the VCA-p 18 or VCA-p40 protein, encoded within the EBV open reading frames BFRF3 and BdRF1 respectively, and fragments thereof, immunochemically reactive with antibodies to the Epstein Barr Virus. Part of the invention is therefore peptides with 176 and 345 amino acids, respectively, and an amino acid sequence as shown in SEQ ID NO: 2 and 4, which are immunochemically reactive with EBV antibodies.

The peptides according to the invention are found to be particularly suitable for use in a diagnostic method for the determination of the presence of EBV or EBV antibodies in a sample. Moreover, a peptide according to the invention may be used in suitable pharmaceutical dosage forms in the treatment of an EBV-related disease. The preparation of vaccines thus obtained, which contain a peptide or fragment thereof as an active ingredient, is known to one skilled in the art.

In contrast to the natural EBV, the peptides according to the invention have the great advantage that they are of a safe, non-infectious origin.

The invention also comprises fragments of said peptides, which are still immunochemically reactive with antibodies to the Epstein-Barr Virus.

BRIEF DESCRIPTION OF THE DRAWINGS

FIGS. 2(a–d):

The above blots were probed with a set of individual sera. Sera used in lanes 1–16 of the blots were respectively:
1. mouse monoclonal antibody to β-Gal (Promega);
2. mouse monoclonal antibody to VCA-P40 raised by immunizing with natural viral capsid proteins (EBV.OT41A);
3. Human antibody mono-specific for viral VCA-P18 obtained by specific immunoaffinity purification with viral VCA-P18;
4–5 Human EBV-seronegative sera; and
6–16 Human EBV-seropositive sera with a different relative reactivity towards viral VCA-P18 and VCA-P40.

Figure 3:
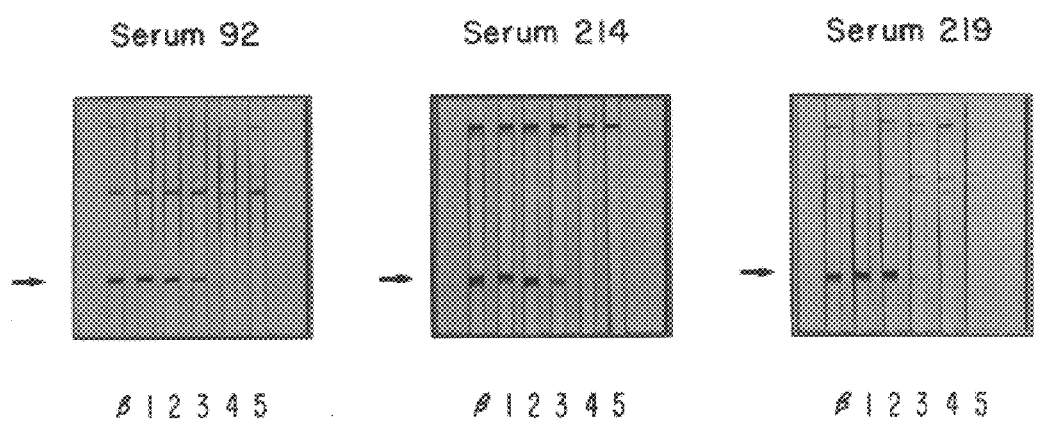

FIG. 3: Immunoblots of three human sera (serum 92, serum 214 and serum 219) on nitrocellulose strips pre-absorbed with the following amounts of BFRF3-β-galactosidase fusion protein:
lane 1: 0 μg BFRF3-β-galactosidase
lane 2: 0.01 μg BFRF3-β-galactosidase
lane 3: 0.1 μg BFRF3-β-galactosidase
lane 4: 0.5 μg BFRF3-β-galactosidase
lane 5: 1 μg BFRF3-β-galactosidase
The lane in which β-galactosidase only is present is indicated as lane β.

Figure 4:
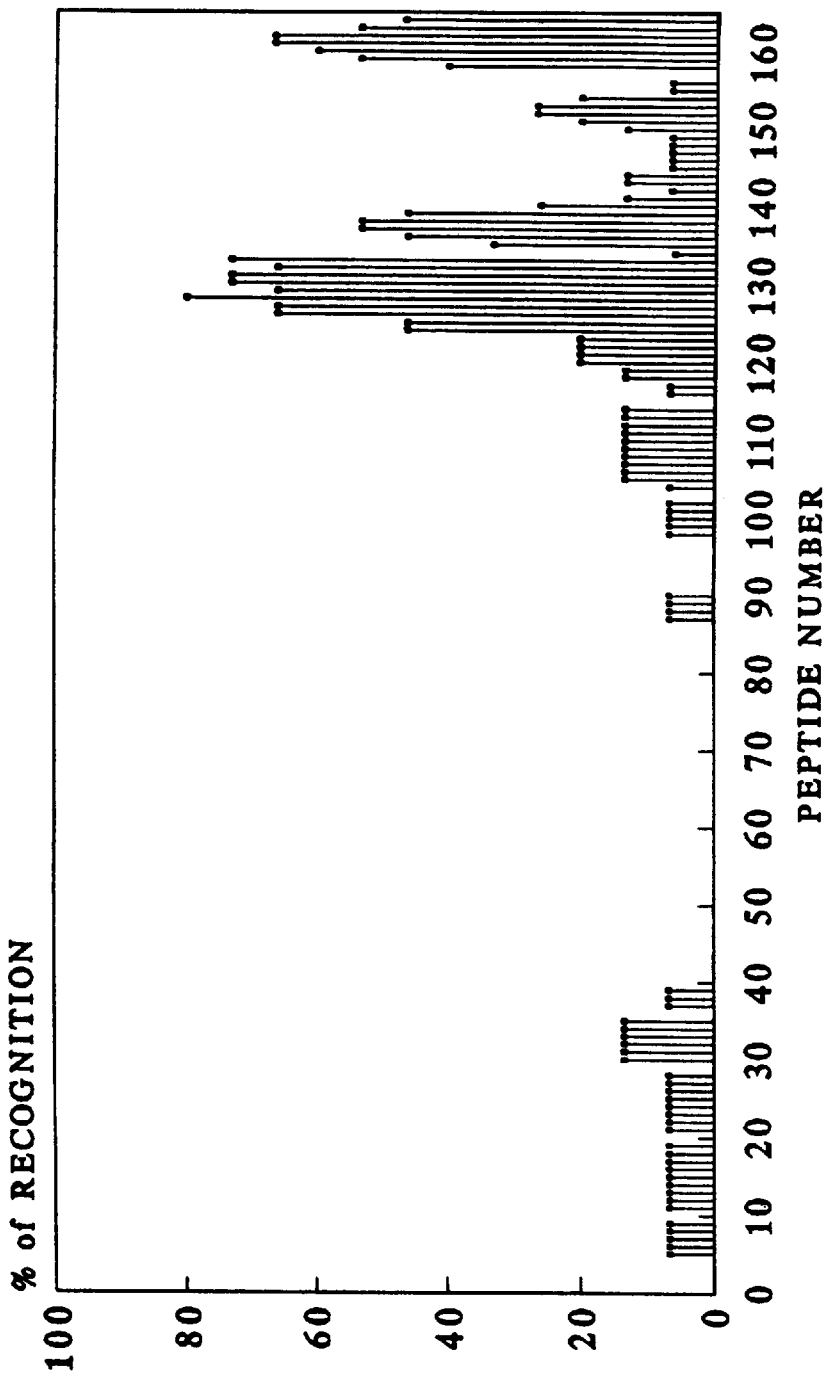

FIG. 4: Results of PEPSCAN analysis: Percentage of 15 human sera from healthy EBV-seropositive donors reactive with 12-mer peptides from the VCA-18 sequence. Starting positions of the 12-mer peptides within the amino acid sequence of the VCA-p18 protein are indicated on the X-axis.

FIGS. 5a and 5b:
PEPSCAN results (optical density at 450 nm) of an analysis of VCA-p18 derived 12-mer peptides, using two rat monoclonal antibodies directed against VCA-p18 (EBV.OT15E and EBV.OT15I respectively).

Figure 6:
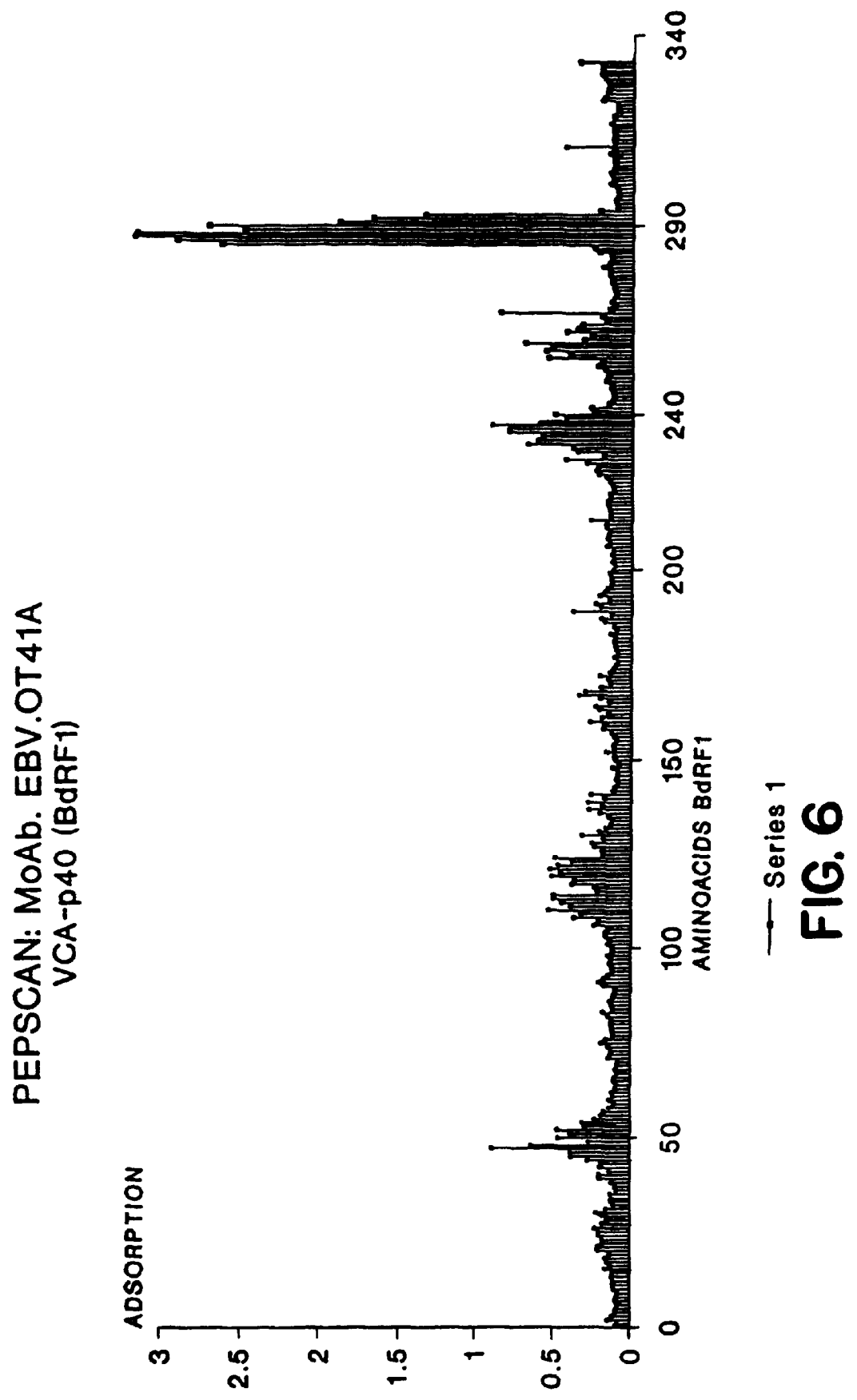

FIG. 6:
PEPSCAN results of an analysis of 12-mer peptides derived form the VCA-p40 protein with a mouse monoclonal antibody (EBV.OT41A) directed against VCA-p40.

Figure 7:
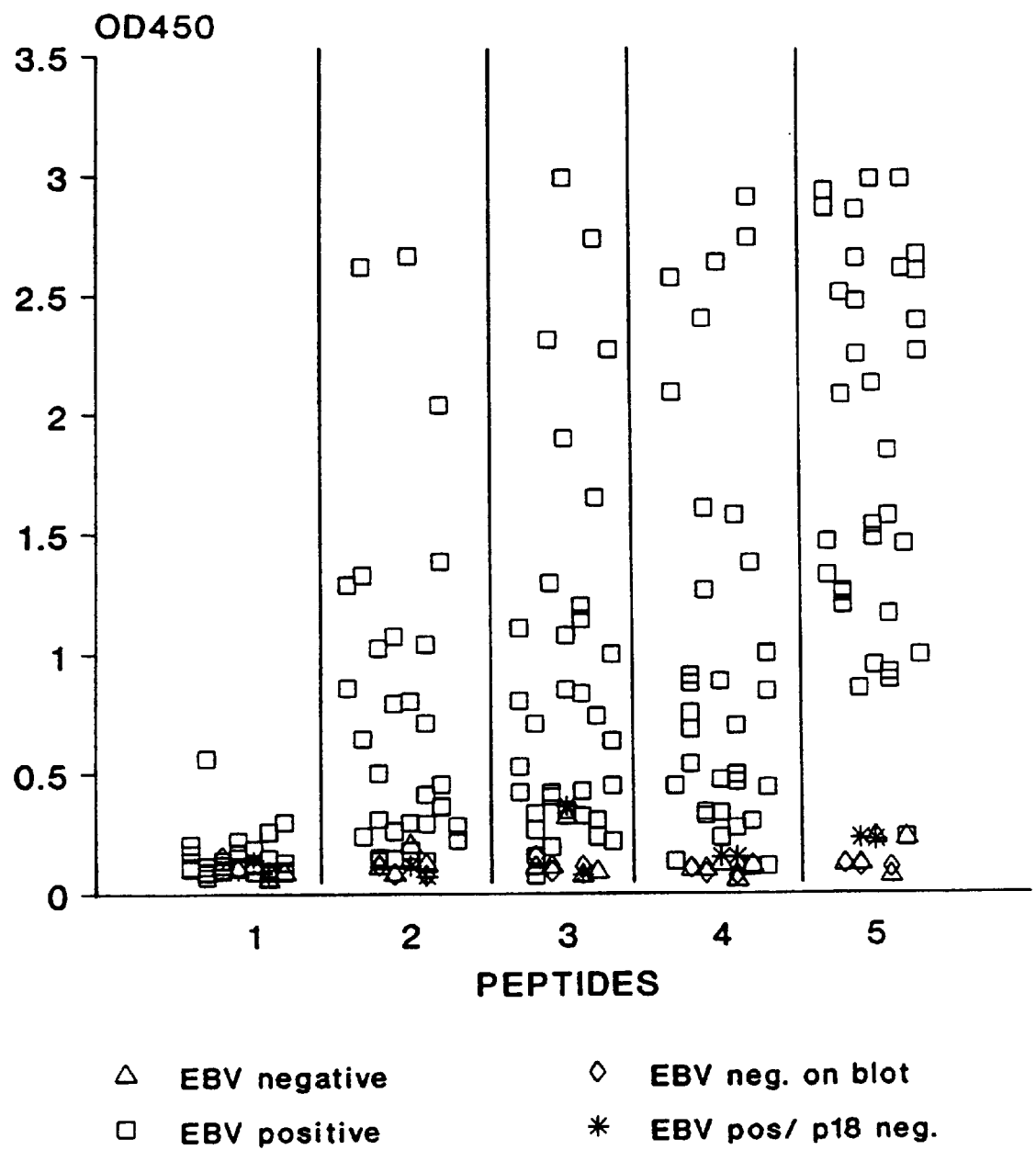

FIG. 7:
ELISA reactivity (optical density at 450 nm) of 43 human serum samples obtained from healthy blood donors tested for IgG-reactivity against selected synthetic peptides derived from the BFRF3-encoded VCA-p18 protein.
Δ indicates sera negative by standard serological analysis
□ indicates sera positive by standard serological analysis
◇ indicates sera indeterminate for EBV antibodies by standard serological analysis but negative on immunoblot.
* indicates sera positive by standard serology but negative for anti-p18 antibodies on immunoblot.
Peptide 1: H$_2$N-GVPRRQRAIDKRQRA-COOH as shown in SEQ ID NO:7
Peptide 2: H$_2$N-GQPHDTAPRGARKKQ-COOH as shown in SEQ ID NO:8
Peptide 3: H$_2$N-AVDTGSGGGGQPHDTAPRGARKKQ-COOH as shown in SEQ ID NO:5
Peptide 4: H$_2$N-STAVAQSATPSVSSSISSLRAATSGATAAA-COOH as shown in SEQ ID NO:6

Peptide 5: Combi-peptide of peptide 4 and 3 linked by S-S-bridging.

Figure 8A:
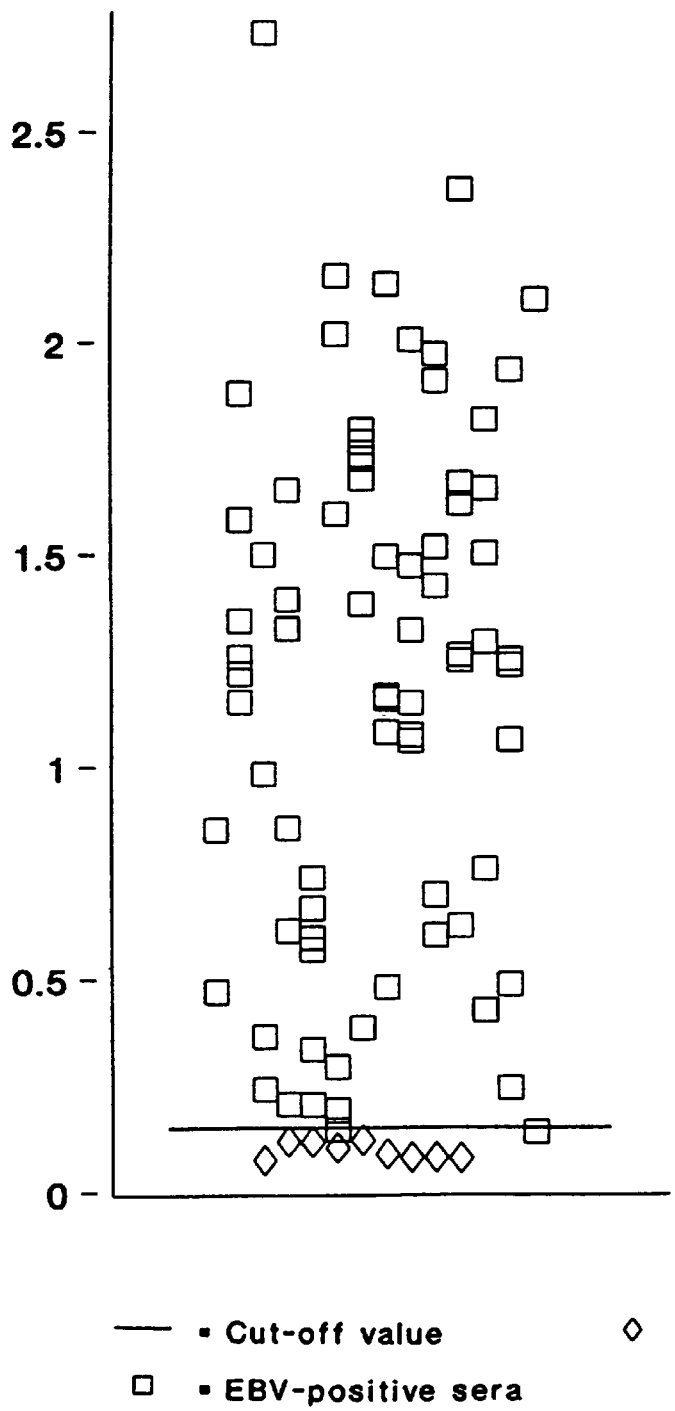

FIGS. 8a, b, c: Analysis of immunoreactivity (ELISA) of the combi-peptide no.5 with:
a) human IgG (76 VCA-I.F. positive sera)
b) human IgM (26 IgM positive sera)
c) human IgA (35 sera from NPC patients)

DETAILED DESCRIPTION OF THE INVENTION

The term "peptide" as used herein refers to a molecular chain of amino acids with a biological activity, and does not refer to a specific length of the product. Thus, inter alia, proteins, fusion proteins or fusion peptides, oligopeptides and polypeptides are included. If required, peptides according to the invention can be modified in vivo or in vitro, for example by glycosylation, amidation, carboxylation or phosphorylation. Functional variants like, for example, acid addition salts, amides, esters, and specifically C-terminal esters, and N-acyl derivatives of the peptides according to the invention are therefore also considered part of the present invention. It will be understood that for the particular proteins or polypeptides embraced herein, natural variations can also exist. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous proteins.

The term "fragment" as used herein means an amino acid sequence comprising a subsequence of a peptide of the invention. Said fragment is a peptide having one or more immunogenic determinants of the VCA-p18 or VCA-p40 protein. Fragments can inter alia be produced by enzymatic cleavage of precursor molecules, using restriction endonucleases for the DNA and proteases for the polypeptides. Other methods include chemical synthesis of the fragments or the expression of peptide fragments by DNA fragments.

Suitable immunogenic fragments of a peptide according to the invention containing (an) epitope(s) can be found by means of the method described in Patent Application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on the Pepscan method, wherein a series of partially overlapping peptides corresponding with partial sequences of the complete polypeptide under consideration, are synthesized and their reactivity with antibodies is investigated. In addition, a number of regions of the peptides can be designated epitopes on the basis of theoretical considerations, although the predictive value of these theoretical considerations is limited. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

Preferred peptides according to the invention are peptides comprising at least one of the amino acid sequences as shown in SEQ ID NO:5 and SEQ ID NO:6.

Most preferred is a peptide comprising the amino acid sequence as shown in SEQ ID NO:5 linked to the amino acid sequence as shown in SEQ ID NO:6. Such a combi-peptide has proven to be extremely useful for the specific detection of IgG, IgA, and IgM antibodies to EBV-VCA, with sensitivity similar to or even better than standard serological techniques. As such, IgM-EBV is a useful diagnostic marker for acute primary EBV infection, whereas IgA to EBV is useful for diagnosis and prognosis in nasopharyngeal carcinoma. EBV-IgG is positive in all human EBV carriers and negative in persons not infected with the virus. In addition, changes in the antibody titer for each of the antibodies of a specific subclass may be of additional diagnostic value.

Since antibodies of different subclasses have a specific diagnostic value in different stages of EBV infection the use of a combi-peptide according to the invention in diagnostic tests, e.g. ELISA, can be of great advantage.

The preparation of the peptides or fragments thereof according to the invention is effected by means of one of the known organic chemical methods for peptide synthesis or with the aid of recombinant DNA techniques.

The organic chemical methods for peptide synthesis are considered to include the coupling of the required amino acids by means of a condensation reaction, either in homogeneous phase or with the aid of a solid phase.

The condensation reaction can be carried out as follows:
a) condensation of a compound (amino acid, peptide) with a free carboxyl group and protected other reactive groups with a compound (amino acid, peptide) with a free amino group and protected other reactive groups, in the presence of a condensation agent;
b) condensation of a compound (amino acid, peptide) with an activated carboxyl group and free or protected other reaction groups with a compound (amino acid, peptide) with a free amino group and free or protected other reactive groups. Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of above-mentioned peptides according to the invention using the "solid phase" is for instance described in J. Amer. Chem. Soc. 85, 2149 (1963) and Int. J. Peptide Protein Res. 35, 161–214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine function.

A particularly suitable solid phase is, for example, the p-alkoxybenzyl alcohol resin (4-hydroxy-methyl-phenoxy-methyl-copolystrene-1% divinylbenzene resin), described by Wang (1974) J. Am. Chem. Soc. 95, 1328. After synthesis, the peptides can be split from this solid phase under mild conditions.

After synthesis of the desired amino acid sequence, detaching of the peptide from the resin follows, for example, with trifluoromethanesulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzene-sulphonyl or p-toluenesulphonyl group, but other groups can also be used, such as substituted or unsubstituted aryl or aralkyl groups, for example benzyl and triphenylmethyl, or groups such as orthonitrophenyl-sulphenyl and 2-benzoyl-1-methyl-vinyl. A particularly suitable α-amino-protective group is, for example, the base-sensitive 9-fluorenyl-methoxycarbonyl (Fmoc) group [Carpino 8& Han (1970) J. Amer. Chem. Soc. 92, 5748].

A more extensive account of possible protecting groups can be found in The Peptides, Analysis, Synthesis, Biology, Vol. 1–9 (Eds. Gross, Udenfriend and Meienhofer) 1979–1987 (Academic Press, Inc.).

It is necessary also to protect the E-amino group of lysine and advisable for the guanidine group of arginine. Customary protective groups in this connection are a Boc group for lysine and a Pmc, Pms, Mbs, or Mtr group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

As already indicated above, the peptides according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide or as a fusion protein with, for example, (part of) β-galactosidase. These types of peptides therefore likewise fall within the scope of the invention. For this purpose, as a constituent of a recombinant DNA, a nucleic acid sequence is used which codes for a peptide according to the invention and which, furthermore, is substantially free from nucleic acid segments, which in the naturally occurring EBV genome flank the nucleic acid sequence indicated above.

This latter method involves the preparation of the desired peptide by means of bringing to expression a recombinant polynucleotide with a nucleic acid sequence which is coding for one or more of the peptides in question in a suitable microorganism as host.

The invention therefore further encompasses nucleic acid sequences encoding a peptide according to the invention, preferably comprising at least part of the nucleic acid sequence as shown in SEQ ID NO: 1 and/or 3.

"Nucleic acid sequence" as used herein refers to a polymeric form of nucleotides of any length, both to ribonucleic acid sequences and to deoxyribonucleic acid sequences. In principle, this term refers to the primary structure of the molecule. Thus, this term includes double- and single-stranded DNA, as well as double- and single-stranded RNA, and modifications thereof.

A nucleic acid sequence according to the present invention can be ligated to various replication effecting DNA sequences with which it is not associated or linked in nature resulting in a recombinant vector molecule which can be used for the transformation of a suitable host. Useful recombinant vector molecules, are preferably derived from, for example, plasmids, bacteriophages, cosmids or viruses. Specific vectors or cloning vehicles which can be used to clone nucleic acid sequences according to the invention are known in the art and include inter alia plasmid vectors such as pBR322, the various pUC, pGEM and Bluescript plasmids, bacteriophages, e.g. kgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule according to the invention are known to those of ordinarily skill in the art and are inter alia set forth in Maniatis, T. et al. (Molecular Cloning A Laboratory Manual, second edition; Cold Spring Harbor Laboratory, 1989). For example, the insertion of the nucleic acid sequence according to the invention into a cloning vector can easily be achieved when both the genes and the desired cloning vehicle have been cut with the same restriction enzyme(s) as complementary DNA termini are thereby produced.

The recombinant vector molecules according to the invention may additionally contain one or more marker activities that may be used to select for desired transformants, such as ampicillin and tetracycline resistance in pBR322, as for example ampicillin resistance and α-peptide of β-galactosidase in pUC8.

The invention also comprises (a) host cell(s) transformed with a nucleic acid sequence or recombinant expression vector molecule described above, capable of producing the peptides according to the invention by expression of the corresponding nucleic acid sequence. A suitable host cell is a microorganism or cell which can be transformed by a nucleic acid sequence encoding a peptide or by a recombinant vector molecule comprising such a nucleic acid sequence and which can, if desired, be used to express said peptide encoded by said nucleic acid sequence. The host cell can be of procaryotic origin, e.g. bacteria such as *Escherichia coli, Bacillus subtilis* and Pseudomonas species; or of eukaryotic origin, such as yeasts, e.g. *Saccharomyces cerevisiae* or higher eukaryotic cells such as insect, plant or mammalian cells, including HeLa cells and Chinese hamster ovary (CHO) cells. In general, prokaryotes are preferred for the construction of the recombinant vector molecules useful in the invention. For expression, nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector molecule comprising a nucleic acid sequence encoding the peptides identified above operably linked to expression control sequences, capable of expressing the DNA sequences contained therein in (a) transformed host cell(s).

It should, of course, be understood that the nucleotide sequences inserted at the selected site of the cloning vector may include only a fragment of the complete nucleic acid sequence encoding for the peptides according to the invention as long as the transformed host will produce a polypeptide having at least one or more immunogenic determinants.

Antibodies directed to a peptide according to the invention are also part of the present invention. The peptides or fragments thereof prepared and described above are used to produce antibodies, both polyclonal and monoclonal. Monoclonal antibodies directed against peptides according to the invention can be readily produced by one skilled in the art.

Preferred antibodies to different epitopes of the VCA-p18 protein according to the invention are antibodies having the same reactivity with VCA-p18 as antibodies produced by the rat-mouse hybridoma cell line deposited at the European Culture of Animal Cell Cultures (ECACC), Porton Down (UK), on Feb. 4, 1993, under the deposit nos. 93020413 or 93020412.

Preferred antibodies to an epitope of the VCA-p40 protein are antibodies having the same reactivity with VCA-p40 as antibodies produced by the mouse-mouse hybridoma cell line deposited at the European Culture of Animal Cell Cultures (ECACC), Porton Down (UK), on Feb. 4, 1993, under the provisional deposit no. 93020414.

Immortalized cell lines capable of excreting monoclonal antibodies according to the invention are also part of the present invention. The preparation of cell lines producing monoclonal antibodies may occur by, for example, by the Kohler and Milstein technique (Kohler and Milstein devised the techniques that resulted in the formation of monoclonal antibody-producing hybridomas (G. Kohler and C. Milstein, 1975, Nature 256:495–497; 1976, Eur. J. Immunol. 6:511–519)), transformation with Epstein-Barr Virus, or a direct transformation technique of B-lymphocytes with oncogenic DNA, or a direct fusion of human B-lymphocytes with a fusion partner being either a human or a mouse-human hybrid myeloma cell line, or a direct fusion of an EBV-transformed B cell line with said myeloma cell lines.

Preferred cell lines according to the invention are the cell lines deposited at the European Collection of Animal Cell Cultures, Porton Down (UK) under deposit nos. 93020413, 93020412, and 93020414. These cell lines were deposited at the ECACC on Feb. 4, 1993, under the terms and conditions of the Budapest Treaty (1977).

The cell lines with deposit nos. 93020413 and 93020412 are both capable of producing monoclonal antibodies (EBV.OT15E and EBV.OT15I respectively) to two respective epitopes of the VCA-p18 protein. These cell lines are rat-mouse hybridoma cell lines. The cell line with provisional deposit no. 93020414 is capable of producing antibodies to an epitope of the VCA-p40 protein, and is a mouse-mouse hybridoma cell line. The antibodies produced by these cell lines have been used to identify epitopes on the respective proteins (as is further exemplified in the examples).

Antibodies, both monoclonal and polyclonal, directed against peptides according to the invention are very suitable in diagnosis and immunocytochemistry for detection in situ in tissue specimen, while those antibodies which are neutralizing are very useful in passive immunotherapy. Especially monoclonal antibodies may be used to raise anti-idiotype antibodies. Techniques for raising anti-idiotype antibodies are known in the art.

Anti-idiotype antibodies reactive with the monoclonal antibodies according to the invention, as described above, are part of the present invention. Anti-idiotype antibodies are antibodies directed to the variable part of immunoglobulins. A subpopulation of anti-idiotype antibodies is known as "anti-idiotype β" or "internal images ". These anti-idiotype βantibodies have either a structural or a three dimensional resemblance with the antigen (Uytdehaag, F. G. C. M. et al. Immunol.Rev; 90; 93–113; 1986). This type of anti-idiotype antibody is widely used as a vaccine against infectious diseases in animal models (Hiernaux J. R.; Infect.Immun.; 56; 1407–1413; 1988, Kennedy, R. C. et al.; Science 232; 220–223; 1986). For use in assays the anti-idiotype antibodies can be raised in large amounts.

Techniques for raising anti-idiotype antibodies are known in the art. For example, anti-idiotype antibodies according to the invention can be obtained by immunizing BALB/c mice with monoclonal antibodies, coupled to KLH with glutaraldehyde according to standard literature procedures, and mixed with Freund's complete adjuvant. The spleen cells of these mice can be immortalized and the thus obtained hybridomas can be screened for anti-idiotype antibody production. Screening of the hybridomas can be performed, for example, by binding monoclonal antibodies according to the invention to a solid phase (wells of microtiter plates) and incubating the solid phase with culture supernatant of growing hybridomas. An EBV peptide coupled to horseradish peroxidase (HRP) can be added. The presence of anti-idiotype antibodies in the culture supernatant will then be indicated by inhibition of the binding of this peptide conjugate to the monoclonal antibodies coated on the solid phase.

Anti-idiotype antibodies can be used, for instance, for inhibiting the binding of human and/or animal EBV antigen in an immunoassay using EBV antibodies. Alternatively anti-idiotype antibodies can be used as a mimicking agent of the immunochemical reagent mentioned hereunder. Said anti-idiotype antibodies are also useful for diagnosis and treatment of EBV, as well as for the elucidation of important epitopic regions of EBV antigens.

An immunochemical reagent comprising one or more peptides or antibodies according to the invention is also part of the present invention. The term "immunochemical reagent" according to the invention usually consists of one more peptides according to the invention and a suitable support or a labelling substance. Supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle, or a carrier protein such as BSA or KLH.

Labelling substances which can be used are, inter alia, a radioactive isotope, a fluorescent compound, an enzyme, a dye sol, metal sol or metal compound as sol particle.

In a method for the detection of antibodies directed against EBV in a sample, an immunochemical reagent according to the invention is brought into contact with the sample. Thereafter, the presence of immune complexes formed between the peptide and antibodies in the sample is detected and by this detection the presence of EBV antibodies in the sample is known and can be determined quantitatively.

Depending on the nature and further characteristics of the immunochemical reagent the immunochemical reaction that takes place is a sandwich reaction, an agglutination reaction, a competition reaction or an inhibition reaction.

For the detection of EBV in a sample an immunochemical reagent according to the invention, containing one or more peptides according to the invention, can be brought into contact with the sample and anti-EBV after which the presence of immune complexes formed can be detected and, from this, the presence of EBV in a sample can be determined.

A particularly suitable method for the detection of EBV in a sample is based on a competition reaction between a peptide according to the invention provided with a labelling substance and an EBV antigen (present in the sample) whereby the peptide and the antigen are competing with the antibody directed against EBV attached to a solid support.

The invention further comprises a method for the detection of Epstein-Barr virus in a sample characterized in that an antibody according to the invention is brought into contact with a sample whereafter the presence of immune complexes formed is detected which is a measure for the presence of Epstein-Barr virus in the sample.

A test kit according to the invention comprises as an essential constituent an immunochemical reagent as described above. Carrying out a sandwich reaction for the detection of EBV antibodies, the test kit may comprise, for example, the peptide according to the invention coated to a solid support, for example the inner wall of a microtest well, and either a labelled peptide according to the invention or a labelled anti-antibody. For carrying out a competition reaction, the test kit may comprise a peptide according to the invention coated to a solid support, and a labelled antibody directed against EBV preferably a monoclonal antibody directed against said peptide. In an agglutination reaction, the test kit comprises an immunochemical reagent which may comprise a peptide according to the invention coated to particles or sols.

Another embodiment of a test kit is, for example, the use of a labelled peptide according to the invention as an immunochemical reagent in a competition reaction with an EBV antigen to be detected for a binding site on the antibody directed against EBV, which is coated to a solid support.

It is within the scope of this invention to use the new nucleotide sequences according to SEQ ID NO:1 and/or 3 as the basis of a test to detect EBV DNA or RNA by a nucleic acid amplification technique, for instance the polymerase chain reaction (PCR) or the nucleic acid sequence based amplification (NASBA), as described in EP 201,814 and EP 329,822, respectively. A method for the amplification and the detection of an Epstein-Barr Virus nucleic acid sequence in a sample using at least one nucleic acid sequence or fragment thereof according to the invention as primer(s) in order to perform a nucleic acid amplification of said Epstein-Barr Virus nucleic acid sequence and to detect the amplified sequence is also part of the present invention. Part of the invention is also a test amplification kit for carrying out above-mentioned amplification technique, said kit containing at least a set of primers corresponding to at least a part of the nucleotide sequences according to the invention.

The invention is further exemplified by the following examples:

EXAMPLE 1

Procedure for isolating and identifying new DNA sequences coding for EBV proteins.

The general strategy followed for the identification resulting in the new EBV marker molecules can be subdivided in the following phases.

1. Identification and production of antibody reagents specifically reactive with the EBV marker molecules.
2. Preparing a cDNA bank from poly-A selected or total cell mRNA, isolated from EBV expressing cells, or preparing a genomic DNA bank from fragments of the viral genome, preferably in phage lambda gt11, followed by screening of the phage synthesized proteins with above antibody reagents.
3. Purification of reactive phages and identification of the EBV-specific insert sequences contained within the genome of the phages.
4. Correlation of the insert sequences with the published prototype EBV genome sequence to locate the corresponding EBV-specified open reading frames.

5. Cloning, expression and production of identified open reading frames in alternative host cells such as E. coli, Baculovirus, yeast or higher eukaryotic cells or alternative expression cq. production systems.

Figure 1:
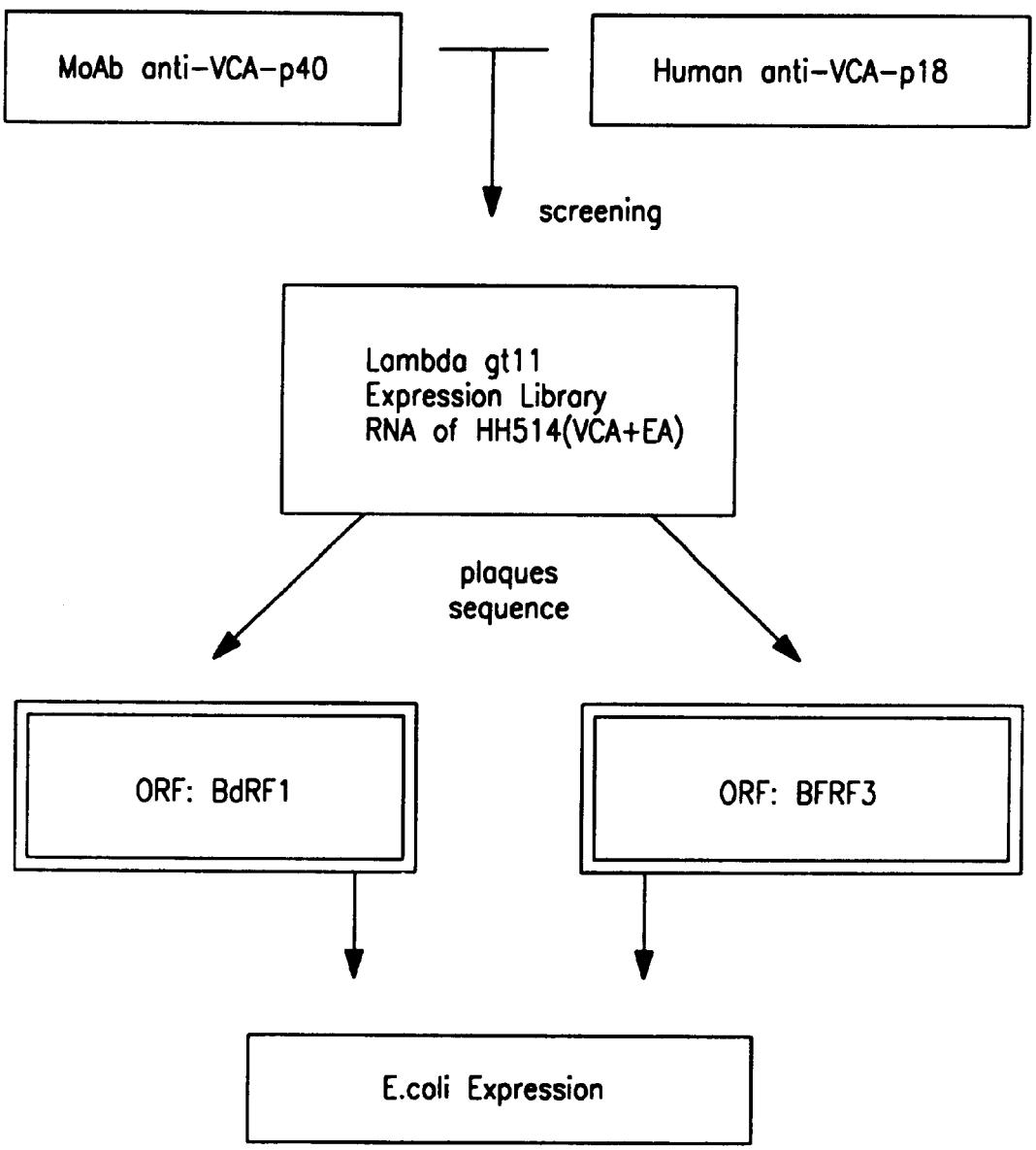
FIG. 1: Outline of the approach used to identify the EBV-encoded genes coding for the VCA-p40 and VCA-p18 proteins.

These procedures are outlined in detail below and illustrated by the scheme as depicted in FIG. 1.

Phase 1

Cell Cultures and Cell Extracts.

The P3HR1-derived cell line HH514.c16 was propagated as a suspension culture in roller bottles and induced for VCA- and EA-expression using 20 ng/ml 12-tetradecanophorbol-13-acetate (TPA) and 3 mM sodium butyrate exactly as described by Middeldorp and Herbrink (J.Virol.Meth., 21, 133–146, 1988). For the selective expression of EA antigens only, viral DNA polymerase was blocked by the addition of 0.5 mM phosphonoacetic acid to the induced cell culture.

Monoclonal Antibodies.

For the production of monoclonal antibodies BALB/c mice were immunized with the nuclear fraction of VCA-induced HH514 cells (F. Wielaard et al., J.Virol.Meth., 21, 105–115, 1988) or with more extensively purified proteins from these cells or form alternative expression systems. Hybridomas were produced according to standard protocols and supernatants were analysed in standard EBV immunofluorescence tests and on immunoblot strips containing antigen extracts from VCA-induced HH514 cells as described by Middeldorp and Herbrink, J.Virol.Meth., 21, 133–146, 1988).

Affinity Purification of Anti-VCA-p18 Antibodies.

Anti-VCA-p18 antibodies were purified from a human EBV-positive serum according to the method of Robinson and Miller (The herpesviruses, Vol.1, 151–192, 1991, Publ.Plenum Publishing Corp. New York) with some minor modifications. In short, following the electrophoretical separation in 10% acrylamide gels, the proteins were blotted onto PVDF membranes (Millipore Corporation, Bedford, USA), and the region on the PVDF membrane corresponding to VCA-p18 was cut out and used as affinity matrix. Nonspecific binding of antibodies to the strips was prevented by incubation overnight in blocking solution (5% dried milk powder, 4% horse serum in phosphate buffered saline, pH 7.4 (PBS)). Thereafter the strips were incubated with diluted human serum (1:25 in blocking solution) for 2 hours. After three wash steps with PBS containing 0.05% Tween 20 the bound antibodies were eluted with 0.1 M glycine, pH 2.7 in two consecutive incubations. The eluate was neutralized with ½₀th volume of 1 M Tris/HCl, pH 9.0. Finally, the eluate was dialyzed against PBS and stored in aliquots at −20° C.

Phase 2

RNA Purification of HH514.c16 Cells.

Total RNA was isolated from induced HH514.c16 cells by the guanidinium/CsCl procedure as described by Maniatis et al. (Molecular cloning: A laboratory manual; Cold Spring Harbor Laboratory, New York, 1982). Purification of poly $(A^+)$ RNA was performed by oligo(dT) chromatography (Pharmacia, Inc., Piscataway N.Y.) as described by Ausubel et al. (Current protocols in molecular biology (1991) Greene Publishing Associates, John Wiley & Sons, New York).

Northern Blot Analysis.

Total RNA (10 μg) was denatured by glyoxal (P. S. Thomas, Methods in Enzymology, 100, 255–266, 1983) and run in agarose gels. After ethidium bromide staining, the separated RNA was vacuum-blotted to nitrocellulose. After 3 hr prehybridization the filter was hybridized overnight at 42° C. with [α-32P]-labeled (Amersham, Bristol, UK) randomly primed or nick translated DNA probes. The hybridization solutions consisted of 50% formamide, 5×SSPE, 5×Denhardts solution (0.1% (w/v) polyvinylpyrrolidone, 0.1% (w/v) BSA, 0.1% (w/v) Ficoll), 0.2 mg sonicated herring sperm DNA per ml and 0.5% SDS. Subsequently, blots were washed and exposed to X-ray film (Eastman Kodak Co., Rochester, N.Y., USA) using intensifying screens.

Construction of cDNA Library in Lambda-gt11.

Five micrograms of poly $(A^+)$-selected RNA was denatured with methylmercury hydroxide. The cDNA synthesis was primed with either oligo(dT) or hexanucleotides. Procedures for first and second-strand synthesis were identical to those described by Gubler and Hoffman (Gene, 25, 263–269, 1983). After EcoRI methylation, EcoRI linker addition and EcoRI digestion, the modified cDNA was size selected by Sepharose CL4B (Pharmacia) chromatography as described in Maniatis et al. cDNA varying in size from 0.5 kB to 3.0 kB was ligated into phosphatase treated lambda-gt11 arms followed by in vitro packaging using the Packagene kit (Promega, San Diego, USA).

Immunological Screening of the Lambda-gt11 Library.

A total of $1 \times 10^4$ recombinant phages of the oligo(dT) primed library and $5 \times 10^5$ recombinants of the hexanucleotide primed library were screened for immunological reactivity (see Maniatis et al.) with affinity purified human anti-p18 antibodies or monoclonal antibody EBV.OT41A. Immunoreactive plaques were detected with alkaline phosphatase-conjugated anti-human or anti-mouse IgG, respectively, as described by the manufacturer (Promega).

Phase 3

Nucleotide Sequence Analysis.

Insert DNA of positive plaques, purified by repeated plaque lifting and immunoscreening, was amplified by the polymerase chain reaction (PCR) technique using primers of the lambda-gt11 flanking sequences containing restriction sites at their 5'-end. After digestion with the appropriate restriction enzyme the DNA fragment was subcloned in pGEM-4Z and sequenced from both sides using a sequence kit (Pharmacia, Upsala, Sweden) which employs a modification on the method of Sanger et al. (Proc.Natl.Acad.Sci., USA, 74, 5463–5467, 1977).

Phase 4

Alignment of Sequences.

Sequences were aligned with the published sequence of EBV B95-8 prototype (Baer et al., Nature 310, 207–211, 1984) as deposited at the EMBL sequence database, using the software programs of the University of Wisconsin, genetics computer group (Gribshov et al. Nucl.Acid res., 14, 327–334, 1986).

Phase 5

Cloning and Expression of BFRF3 and BdRF1 in E.coli.

The EBV genome-encoded open reading frames (ORFs), BFRF3 and BdRF1, were amplified by PCR using viral DNA, purified from virions isolated by sucrose density centrifugation from HH514.c16 culture supernatants as a target. Primers of each set containing restriction sites at their 5'-end were used for cloning the amplified fragment in the EcoRI-HindIII site of expression vector pMLB1113 (a derivative of PBR322) (Zagurski and Berman, Gene, 27, 183–101, 1984) which is located at the fifth codon of the 5' end of the LacZ gene. Proteins expressed from these constructs consist of the first 5 amino acids of β-galactosidase followed by the recombinant protein linked at their C-terminus to the remainder of β-galactosidase. Non-fusion proteins were constructed similarly, but with a stop codon inserted at the 3' end of the insert.

E.coli Expression of Recombinant Proteins.

Transformed E.coli cultures were induced by addition of 1 mM IPTG (isopropyl-β-D-thiogalactopyranoside). At 2 hrs post-induction bacterial cells were collected by centrifugation and suspended in SDS-PAGE sample buffer and analysed by immunoblotting.

EXAMPLE 2

Immunoreactivity of the VCA-p18 and VCA-D40 Proteins.

The immunoreactivity of the proteins obtained following the procedure as outlined in Example 1 was investigated by immunoblot analysis. For this purpose whole cell proteins of either VCA-induced HH514.c16 cells or E.coli expressing BFRF3- or BdRF1-β-galactosidase fusion proteins or β-galactosidase only were separated by SDS-PAGE and blotted onto nitrocellulose. Strips prepared from these blots were incubated with individual sera and antibody preparations.

Immunoblot Procedure:

The immunoblot procedure was performed essentially as described by Middeldorp and Herbrink (J.Virol.Meth., 21 p133–159, 1988) and is briefly outlined below: After SDS-PAGE proteins were transferred to nitrocellulose filters (0.2μ Schleicher & Schuell, Den Bosch, the Netherlands). Non-specific binding of antibodies to the filters was prevented by incubation for at least 1 hr at room temperature (RT) with blocking buffer (4% dried milk powder, 5% horse serum in Tris buffered saline (TBS)). Human sera were diluted to an appropriate dilution in blocking buffer and incubated for at least 1 hr. Blots or strips were washed three times in TBS+0.05% Tween 20 (TBSt), and alkaline phosphatase (AP)-conjugated anti-human IgG antibody (Promega), or HRP-conjugated anti-mouse IgG, or anti-rat IgG (Organon Teknika Cappel, Boxtel, the Netherlands) was added at the appropriate dilution in blocking buffer. After further incubation and rinse steps, the blot was developed using nitroblue tetrazolium (NBT) and 5-bromo-4-chloro-3-indolyl phosphate (BCIP) as substrates for AP and 4-chloronaphtol for HRP.

The resulting blots are depicted in FIGS. 2a–d.

Sera used in lanes 1–12 of the blots were respectively:
1. mouse monoclonal antibody to β-Gal (Promega);
2. mouse monoclonal antibody to VCA-P40 raised by immunizing with natural viral capsid proteins (EBV.OT41A);
3. Human antibody mono-specific for viral VCA-P18 obtained by specific immunoaffinity purification with viral VCA-P18;

4–5 Human EBV-seronegative sera; and

6–16 Human EBV-seropositive sera with a different relative reactivity towards viral VCA-P18 and VCA-P40.

Figure 2A:
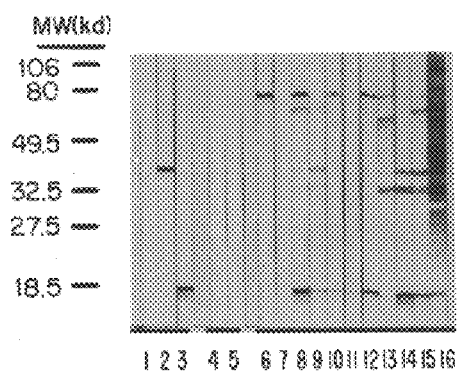
FIG. 2a): Western blot of nuclear antigen extract of virus-producer cell line HH514, induced for expression of EA and VCA.

FIG. 2a shows immunoreactivity of the natural viral polypeptides, separated by reducing SDS-PAGE in 12.5% acrylamide. Anti-β-galactosidase antibodies are negative (1), whereas anti-sera specific for VCA-p40 (2) and VCA-p18 (3) react with the respective viral proteins. Strips 4 and 5, stained with human EBV-negative sera, show no reactivity, whereas strips 6–16 represent different immunoreactivities with EBV proteins as found in normal healthy seropositive blood donors (6–15) or patients with active EBV disease (16). Positions of the VCA-p18 and VCA-p40 bands are indicated on the right hand side.

Figure 2B:
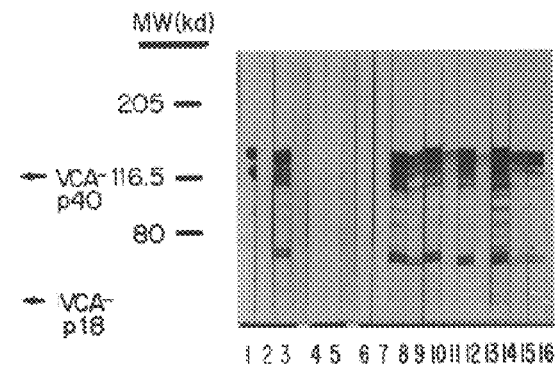
FIG. 2b): Western blot of whole cell lysate of E.coli expressing the BFRF3-β-galactosidase fusion protein.

FIG. 2b shows immunoreactivity of whole cell proteins from E.coli expressing the VCA-p18 β-galactosidase fusion protein (BFRF3-LacZ) separated by reducing SDS-PAGE in 10% acrylamide. Anti-β-galactosidase (1) and anti VCA-p18 (3) antibodies specifically react with a number of protein bands which are due to proteolytic fragmentation in E.coli of the original fusion protein at 134 kDa. The anti-VCA-p40 monoclonal antibody (2) is negative, just like human EBV-negative sera (4–5). Human sera with different reactivites to viral VCA-p18 show similar different reactivities on the fusion protein. Again staining of multiple bands are due to proteolytic breakdown of the fusion protein in E.coli.

Figure 2C:
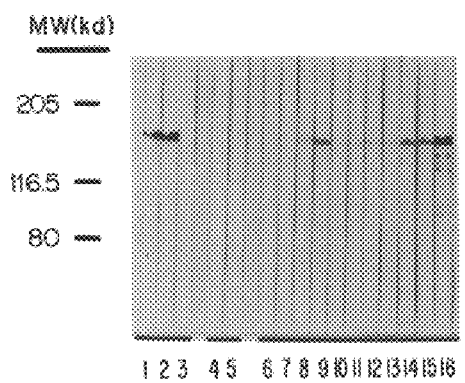
FIG. 2c): Western blot of whole cell lysate of E.coli expressing the BdRF1-β-galactosidase fusion protein.
Figure 2D:
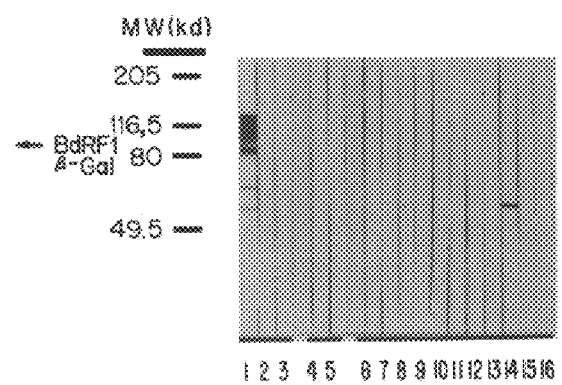
FIG. 2d): Western blot of whole cell lysate of E.coli expressing β-galactosidase only.

FIG. 2c shows the same analysis for the VCA-p40-β-galactosidase fusion protein in E coli, which is less sensitive to proteolysis resulting in a single band at 156 kDa. Interpretation of FIG. 2c is analogous to 2b. FIG. 2d represents a control blot of E.coli expressing β-galactosidase only.

From the above described study it is apparent that the individual E.coli constructs indeed express the respective fusion proteins. Human sera show the same reactivity towards the expressed proteins as towards the natural viral proteins.

EXAMPLE 3

Immunoadsorption.

Immunochemical identity of an alternative peptide according to the invention and the corresponding natural viral protein can be proven by pre-absorption of human sera, reactive on immunoblots containing natural viral protein(s), with different concentrations of the peptide according to the invention, resulting in the disappearance of specific antibody reactivity to the corresponding natural viral protein on the blot. In addition to proving immunochemical identity, this technique provides strong evidence that immunoreactivity of a viral protein on immunoblots is mediated by antibody binding to a single (dominant) protein species.

An experiment as described above was performed for the VCA-p18 marker protein:

The immunoreactivity of human sera, (serum 92, serum 214 and serum 219), obtained from three healthy EBV-seropositive donors, was studied by immunoblot analysis on nitrocellulose strips containing nuclear antigens from VCA-induced HH514 cells, separated by reducing SDS-PAGE in 10% acrylamide gels. Sera were preabsorbed overnight at +4° C. with increasing amounts of purified BFRF3-β-galactosidase fusion protein, or with β-galactosidase only before immunoblot analysis. (Staining for IgG-reactivity was performed with peroxidase-labeled sheep anti-human IgG), using N-chloronaphtol as precipitating substrate.

The results of this experiment are illustrated by FIG. 3. The amounts of purified BFRF3-β-galactosidase fusion protein used in pre-absorption of 1 ml 1:100 diluted serum analysed in the respective lanes of the immunoblots as depicted in FIG. 3 were:

lane 1: 0 μg BFRF3-β-galactosidase
lane 2: 0.01 μg BFRF3-β-galactosidase
lane 3: 0.1 μg BFRF3-β-galactosidase
lane 4: 0.5 μg BFRF3-β-galactosidase
lane 5: 1 βg BFRF3-β-galactosidase
The lane in which only β-galactosidase was used for pre-absorption is indicated as lane β.

From FIG. 3 it can be seen that reactivity of the band representing VCA-p18 (arrow) disappears with increasing concentrations of BFRF3β-galactosidase fusion protein during preabsorption. Preabsorption with β-galactosidase alone had no effect, whereas reactivity with other EBV proteins is not affected by any of the preabsorptions. Staining of non-related proteins (e.g. EBNA, at 72 kD or VCA-p40 at 40 kD) is not affected.

From the above described experiment it is apparent that immunostaining of viral VCA-p18 by human serum antibodies is specifically inhibited by preabsorption of these sera with BFRF3 fusion proteins, proving the immunochemical identity of VCA-p18 and the protein encoded by the BFRF3 reading frame. These experiments also indicate that reactivity of human sera with VCA-p18 is caused by interaction with a single viral protein.

EXAMPLE 4
Localization of Immunoreactive Epitopes by PEPSCAN.
Peptide Synthesis and Immunoscreening (PEPSCAN).

most reactive peptide within domain I, which peptide is indicated in lane 3. Lane 4 and 5 represent similar data for domain II and III.

TABLE 1

Immunological response of 15 EBV VCA-p18 positive sera. (Only the response of the most reactive peptide located in the important epitope domains of VCA-p18 are illustrated).

| | Domain I (pept 120–140) | | Domain II (pept. 152–155) | | Domain III pept. 159–165 | |
|---|---|---|---|---|---|---|
| Serum No. | Elisa $OD_{450}$ | Peptide A.A.-sequence | Elisa $OD_{450}$ | Peptide A.A.-sequence | Elisa $OD_{450}$ | Peptide A.A.-sequence |
| 1 | 1.418 | 120-TAVAQSATPSVS-132 (SEQ ID NO: 9) | — | — | — | — |
| 2 | 1.820 | 120-TAVAQSATPSVS-132 (SEQ ID NO: 9) | 0.678 | 155-DTGSGGGGQPHD-167 (SEQ ID NO: 19) | 0.423 | 162-GQPHDTAPRGAR-174 (SEQ ID NO: 21) |
| 3 | 1.228 | 128-PSVSSSISSLRA-140 (SEQ ID NO: 10) | — | — | 0.808 | 162-GQPHDTAPHGAR-174 (SEQ ID NO: 21) |
| 4 | 1.230 | 128-PSVSSSISSLRA-140 (SEQ ID NO: 10) | — | — | 0.761 | 162-GQPHDTAPRGAR-174 (SEQ ID NO: 21) |
| 5 | 0.540 | 128-PSVSSSISSLRA-140 (SEQ ID NO: 10) | — | — | 1.354 | 162-GQPHDTAPRGAR-174 (SEQ ID NO: 21) |
| 6 | 0.731 | 129-SVSSSISSLRAA-141 (SEQ ID NO: 11) | — | — | 1.441 | 162-GQPHDTAPRGAR-174 (SEQ ID NO: 21) |
| 7 | 0.385 | 129-SVSSSISSLRAA-141 (SEQ ID NO: 11) | — | — | 0.770 | 163-QPHDTAPRGARK-175 (SEQ ID NO: 22) |
| 8 | 1.360 | 131-SSSISSLRAATS-143 (SEQ ID NO: 12) | — | — | 1.343 | 160-GGGQPHDTAPRG-172 (SEQ ID NO: 20) |
| 9 | 1.598 | 131-SSSISSLRAATS-143 (SEQ ID NO: 12) | 0.510 | 153-AVDTGSGGGGQP-165 (SEQ ID NO:17) | 1.481 | 162-GQPHDTAPRGAR-174 (SEQ ID NO: 21) |
| 10 | 1.591 | 131-SSSISSLRAATS-143 (SEQ ID NO: 12) | 0.474 | 153-AVDTGSGGGGQP-165 (SEQ ID NO:17) | 1.481 | 162-GQPHDTAPRGAR-174 (SEQ ID NO: 21) |
| 11 | 1.251 | 131-SSSISSLRAATS-143 (SEQ ID NO: 12) | 0.958 | 152-AAVDTGSGGGGQ-164 (SEQ ID NO:16) | 0.774 | 162-GQPHDTAPRGAR-174 (SEQ ID NO: 21) |
| 12 | 1.839 | 133-SISSLRAATSGA-145 (SEQ ID NO: 13) | — | — | 0.407 | 162-GQPHDTAPRGAR-174 (SEQ ID NO: 21) |
| 13 | 1.128 | 134-ISSLRAATSGAT-146 (SEQ ID NO: 14) | 0.460 | 154-VDTGSGGGGQPH-166 (SEQ ID NO:18) | 1.535 | 162-GQPHDTAPRGAR-174 (SEQ ID NO: 21) |
| 14 | 1.064 | 138-RAATSGATAAAS-150 (SEQ ID NO: 15) | — | — | 1.319 | 162-GQPHDTAPRGAR-174 (SEQ ID NO: 21) |
| 15 | 0.695 | 138-RAATSGATAAAS-150 (SEQ ID NO: 15) | — | — | 0.644 | 162-GQPHDTAPHGAR-174 (SEQ ID NO: 21) |

Peptides with a length of 12 amino acids (AA) and an overlap of 11 AA of the AA sequence of ORF BFRF3 and BdRF1 were synthesized by automated solid phase peptide synthesis onto chemically activated polyethylene pins as originally described by Geijsen et al. (Proc.Nat.Acad.Sci., USA, 83, 3998–4002, 1984). The immunoreactivity for EBV-specific antibodies, using 15 sera from healthy EBV seropositive donors was determined as described by Middeldorp and Meloen (J.Virol.meth., 21, 147–159, 1988). The results of PEPSCAN analysis of 12 AA peptides derived from the VCA-p18 sequence are depicted in FIG. 4. The numbers on the X-axis represent the starting position on the VCA-p18 sequence of each 12-mer peptide analysed. Indicated on the Y-axis in FIG. 4 is the percentage of human sera reactive with a certain 12-mer peptide of the VCA-p18 protein encoded in the BFRF3 reading frame. Positive reaction is defined at 3 times the Standard Deviation above the mean reactivity of EBV-seronegative human serum on the same set of pins. From FIG. 4 three immunodominant domains can be defined: Domain I: AA 120–140, Domain II: AA152–155, Domain III: AA 159–165. (These numbers again indicate the starting position of the 12-mer peptides used for PEPSCAN). Table 1 gives a detailed description of the most reactive peptides for each individual serum used in this study. In the first lane of Table 1 the number of the individual sera is indicated. The second lane indicates the PEPSCAN OD450 value (Optical Density at 450 nm) for the

EXAMPLE 5
PEPSCAN Analysis with Rat and Mouse Monoclonal Antibodies Directed Against BFRF3-encoded VCA-p18 protein, or the BdRF1 -encoded VCA-p40 protein.

PEPSCAN analysis was performed, in a way similar to the procedure described in Example 4, for human sera, to delineate the position of linear epitopes detected by monoclonal antibodies.

FIGS. 5a and 5b show the PEPSCAN results of such an analysis using two rat monoclonal antibodies directed against VCA-p18 (EBV.OT15E and EBV.OT15I respectively), each detecting a different linear epitope.

FIG. 6 shows the PEPSCAN results for a mouse monoclonal antibody (EBV.OT41A) directed against VCA-p40 encoded by the BdRF1 reading frame. Cross analysis of the two rat monoclonals on the VCA-p40 (BdRF1) sequence and vice-versa of the mouse monoclonal on the VCA-p18 (BFRF3) sequence gave clear negative results.

From FIG. 6 it is apparent that EBV.OT41 A recognizes a distinct linear epitope in the C-terminal region of the VCA-p40 protein.

EXAMPLE 6
Selection of Synthetic Peptides Derived from the BFRF3-encoded VCA-p18 Protein by Computer Analysis and PEPSCAN, and Analysis of Immunoreactivity of these Peptides with Normal Human Donor Sera.

Synthetic peptides were made by standard solid phase synthesis using t-BOC chemistry. Peptides from BFRF3- encoded VCA-p18 protein were selected either on the basis of predicted high antigenicity using the computer program "antigenic index" developed by Jameson and Wolf (CABIOS 4, 181–186, 1988) [peptides 1 and 2 in FIG. 7 were selected on this basis] or on the basis of functional high antigen reactivity in PEPSCAN as described in Example 4. [Peptides 3 and 4 in FIG. 7 were selected on this basis, representing domain I plus II and domain III from Table 1.] In addition, a combi-peptide was made (peptide 5 in FIG. 7) which represents a combination of the three most reactive domains identified by PEPSCAN, leaving out those peptide regions which show low PEPSCAN reactivity.

Peptides 1–5 with amino acid sequences as indicated below were coated onto the solid phase, i.e. the wells of polystyrene microtiter plates, at 1 µg per ml in 0.05M $NHCO_3$ buffer at pH 9.6 overnight at 4° C. After washing twice with Phosphate-buffered saline (PBS) at pH7.4 the wells were filled with 100 µl of human serum, diluted 1:100 in PBS containing 0.05% Tween 20 (PBST) and incubated for 1 hour at 37° C. After three PBS-T washes HRP labeled sheep anti-human IgG antibodies were added at the appropriate dilution in PBS-T and incubated for 1 hr at 37° C. After three PBS-T washes, bound enzyme activity was detected using tetramethylbenzidine as substrate. The reaction was stopped at 30 minutes by adding 100 µl 1 M $H_2SO_4$. The absorbance was measured at 450 nm using a Multiscan photometer. Sera were tested for EBV antibodies using standard immunofluorescence serology or immunoblot analysis as described before. Peptides used were:

Peptide 1: $H_2N$-GVPRRQRAIDKRQRA-COOH as shown in SEQ ID NO:7

Peptide 2: $H_2N$-GQPHDTAPRGARKKQ-COOH as shown in SEQ ID NO:8

Peptide 3: $H_2N$-AVDTGSGGGGQPHDTAPRGARKKQ-COOH as shown in SEQ ID NO:5

Peptide 4: $H_2N$-STAVAQSATPSVSSSISSLRAATSGATAAA-COOH as shown in SEQ ID NO:6

Peptide 5: Combi-peptide of peptide 4 and 3 linked by S-S-bridging, using extra cysteine residues at the C-terminus of peptide 4 and the N-terminus of peptide 3.

FIG. 7 shows the results of ELISA experiments using peptides 1–5 coated onto the solid phase and a random panel of sera from human healthy blood donors used at 1:100 dilution according to standard procedures.

Subsequently these sera were tested by immunoblot for the reactivity with viral VCA-p18.

From these experiments it is apparent that computer prediction based upon the "antigenic index" program have no predictive value with respect to the immunogenicity towards sera from naturally infected individuals as almost all sera were negative with peptide 1, while peptide 2 is reactive with only about 50% of the sera tested.

Peptides selected on the basis of PEPSCAN show good reactivity with 60–80% of the sera tested respectively. Surprisingly the combi-peptide combining peptides 3 and 4 shows 95% reactivity with human sera. P18 immunoblot negative sera do not show any reactivity with the selected peptides.

EXAMPLE 7

Reactivity of Combi-peptide 5, Derived from the BFRF3-encoded VCA-p18 Protein, with Human Serum Antibodies of Different Subclasses.

The combi-peptide 5, with the amino acid sequence as described in Example 6, was used to analyse the reactivity of human serum immunoglobulins of different subclasses by means of ELISA (procedure as described in Example 6). In all cases combi-peptide 5 was used on the solid phase exactly as described in Example 6. Antibody reactivity was detected as described in Example 6 using 1:100 diluted sera. Results are shown in FIG. 8. IgM reactivity was detected in human sera pre-absorbed with Gull-Sorb (Gull Laboratories Inc., Salt Lake City, Utah, USA) according to the instructions of the manufacturer, in order to inhibit IgG-reactivity. IgM antibodies were detected with HRP-labeled sheep anti-human IgM antibodies specific for the heavy chain of human IgM.

IgA reactivity was also detected in Gull Sorb treated sera using anti-IgA specific HRP labeled second antibodies. Sera for FIG. 8a (IgG) were obtained from 76 healthy seropositive blood donors, positive for VCA-IgG by standard serology and 9 donors negative for EBV antibodies.

Sera for FIG. 8b (IgM) were obtained from 26 mononucleosis patients positive for VCA-IgM by standard serology and 18 healthy donors negative for VCA-IgM but positive for VCA-IgG.

Figure 8C:
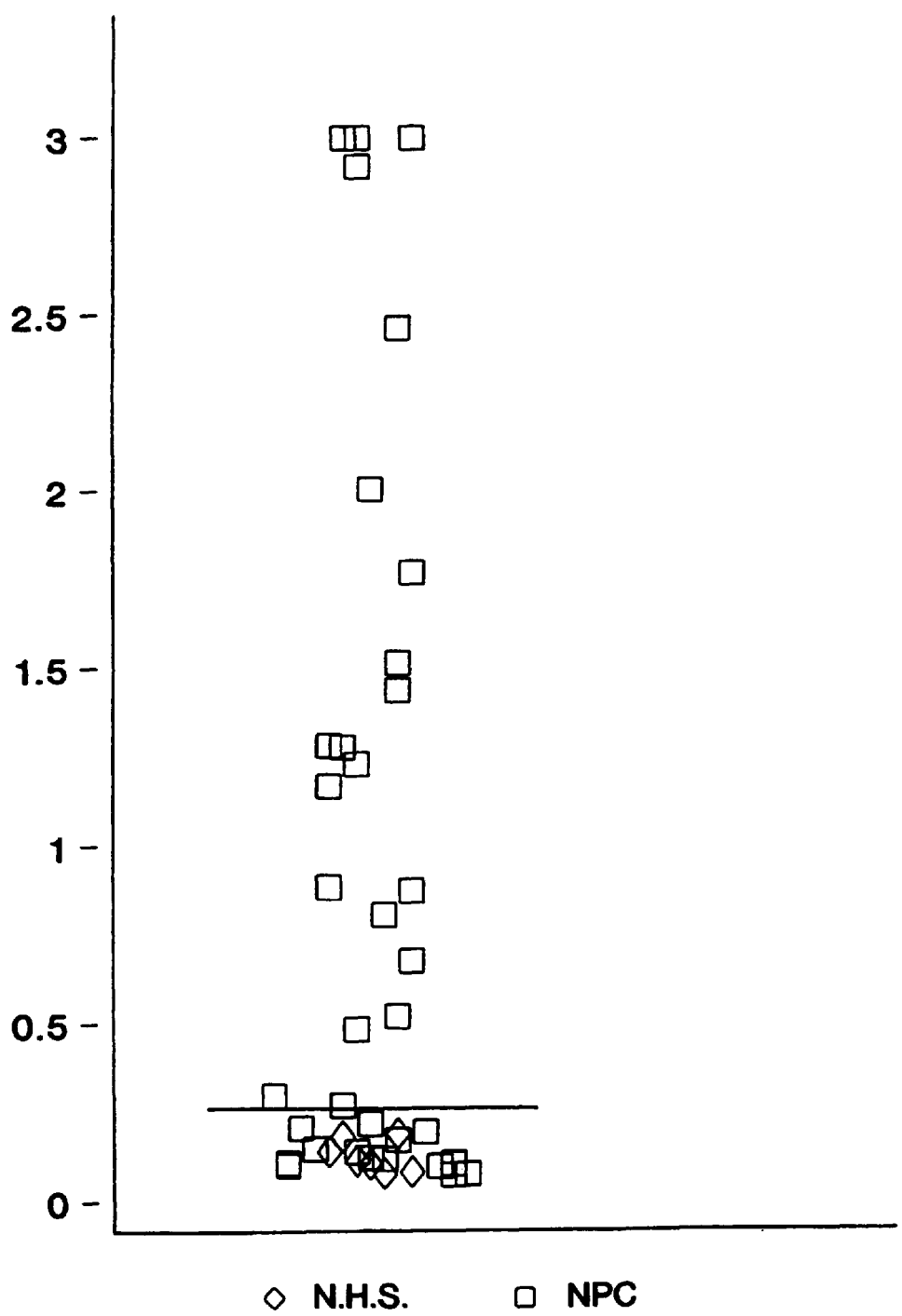

Sera for FIG. 8c (IgA) were obtained from 35 confirmed nasopharyngeal carcinoma patients from whom no IgA-specific data were available, but all of which were IgG-VCA positive and from 7 healthy VCA-IgG positive donors.

From the above experiments it can be seen that the VCA-p18 derived combi-peptide can be used for specific detection of IgG, IgM and IgA antibodies to EBV-VCA, with sensitivity similar or better then standard serological techniques. EBV-negative sera are negative in all cases.

We claim:

1. A monoclonal antibody, which is monoclonal antibody EBV.OT15E.

2. Monoclonal antibody EBV.OT41A.

3. An immortalized cell line, which is selected from the group consisting of the cell lines deposited with the European Collection of Animal Cell Cultures (ECACC) under deposit No. 93020413 and deposit No. 93020412.

4. Monoclonal antibody EBV.OT15I.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 538 base pairs
      (B) TYPE: nucleic acid
      (C) STRANDEDNESS: double
      (D) TOPOLOGY: unknown (ii) MOLECULE TYPE: DNA (genomic)

(vi) ORIGINAL SOURCE:
      (A) ORGANISM: Epstein-Barr virus (xi) SEQUENCE DESCRIPTION: SEQ ID NO: 1:

```
CATGATGGCA CGCCGGCTGC CCAAGCCCAC CCTCCAGGGG AGGCTGGAGG CGGATTTTCC        60

AGACAGTCCC CTGCTTCCTA AATTTCAAGA GCTGAACCAG AATAATCTCC CCAATGATGT       120

TTTTCGGGAG GCTCAAAGAA GTTACCTGGT ATTTCTGACA TCCCAGTTCT GCTACGAAGA       180

GTACGTGCAG AGGACTTTTG GGGTGCCTCG GCGCCAACGC GCCATAGACA AGAGGCAGAG       240

AGCCAGTGTG GCTGGGGCTG GTGCTCATGC ACACCTTGGC GGGTCATCCG CCACCCCGT       300

CCAGCAGGCT CAGGCCGCCG CATCCGCTGG GACCGGGGCC TTGGCATCAT CAGCGCCGTC       360

CACGGCCGTA GCCCAGTCCG CGACCCCTC TGTTTCTTCA TCTATTAGCA GCCTCCGGGC        420

CGCGACTTCG GGGCGACTG CCGCCGCCTC CGCCGCCGCA GCCGTCGATA CCGGGTCAGG        480

TGGCGGGGA CAACCCCACG ACACCGCCCC ACGCGGGGCA CGTAAGAAAC AGTAGCCC          538
```

(2) INFORMATION FOR SEQ ID NO: 2:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 2:

```
Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
                20                  25                  30

Asn Asn Leu Pro Asn Asp Val Phe Arg Glu Ala Gln Arg Ser Tyr Leu
            35                  40                  45

Val Phe Leu Thr Ser Gln Phe Cys Tyr Glu Glu Tyr Val Gln Arg Thr
        50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ser Ala Gly Thr Gly Ala
                100                 105                 110

Leu Ala Ser Ser Ala Pro Ser Thr Ala Val Ala Gln Ser Ala Thr Pro
            115                 120                 125

Ser Val Ser Ser Ile Ser Ser Leu Arg Ala Ala Thr Ser Gly Ala
        130                 135                 140

Thr Ala Ala Ser Ala Ala Ala Ala Val Asp Thr Gly Ser Gly Gly
145                 150                 155             160

Gly Gly Gln Pro His Asp Thr Ala Pro Arg Gly Ala Arg Lys Lys Gln
                165                 170                 175
```

(2) INFORMATION FOR SEQ ID NO: 3:

(i) SEQUENCE CHARACTERISTICS:
        (A) LENGTH: 1038 base pairs
        (B) TYPE: nucleic acid
        (C) STRANDEDNESS: double
        (D) TOPOLOGY: unknown (ii) MOLECULE TYPE: DNA (genomic)

(vi) ORIGINAL SOURCE:

(A) ORGANISM: Epstein-Barr virus (xi) SEQUENCE DESCRIPTION: SEQ ID NO: 3:

```
ATGCTATCAG GTAACGCAGG AGAAGGAGCA ACAGCCTGCG GAGGTTCGGC CGCCGCGGGC          60

CAGGACCTCA TCAGCGTCCC CCGCAACACC TTTATGACAC TGCTTCAGAC CAACCTGGAC         120

AACAAACCGC CGAGGCAGAC CCCGCTACCC TACGCGGCCC CGCTGCCCCC CTTTTCCCAC         180

CAGGCAATAG CCACCGCGCC TTCCTACGGT CCTGGGGCCG GAGCGGTCGC CCCGGCCGGC         240

GGCTACTTTA CCTCCCCAGG AGGTTACTAC GCCGGGCCCG CGGGCGGGGA CCCGGGTGCC         300

TTCTTGGCGA TGGACGCTCA CACCTACCAC CCCCACCCAC ACCCCCCTCC GGCCTACTTT         360

GGCTTGCCGG GCCTCTTTGG CCCCCCTCCA CCCGTGCCTC CTTACTACGG ATCCCACTTG         420

CGGGCAGACT ACGTCCCCGC TCCCTCGCGA TCCAACAAGC GGAAAAGAGA CCCCGAGGAG         480

GATGAAGAAG GCGGGGGGCT ATTCCCGGGG GAGGACGCCA CCCTCTACCG CAAGGACATA         540

GCGGGCCTCT CCAAGAGTGT GAATGAGTTA CAGCACACGC TACAGGCCCT GCGCCGGGAG         600

ACGCTGTCCT ACGGCCACAC CGGAGTCGGA TACTGCCCCC AGCAGGGCCC CTGCTACACC         660

CACTCGGGGC CTTACGGATT TCAGCCTCAT CAAAGCTACG AAGTGCCCAG ATACGTCCCT         720

CATCCGCCCC CACCACCAAC TTCTCACCAG GCAGCTCAGG CGCAGCCTCC ACCCCCGGGC         780

ACACAGGCCC CCGAAGCCCA CTGTGTGGCC GAGTCCACGA TCCCTGAGGC GGGAGCAGCC         840

GGGAACTCTG ACCCCGGGA GGACACCAAC CCTCAGCAGC CCACCACCGA GGGCCACCAC         900

CGCGGAAAGA AACTGGTGCA GGCCTCTGCG TCCGGAGTGG CTCAGTCTAA GGAGCCCACC         960

ACCCCCAAGG CCAAGTCTGT GTCAGCCCAC CTCAAGTCCA TCTTTTGCGA GGAATTGCTG        1020

AATAAACGCG TGGCTTGA                                                     1038
```

(2) INFORMATION FOR SEQ ID NO: 4:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 4:

```
Met Leu Ser Gly Asn Ala Gly Glu Gly Ala Thr Ala Cys Gly Gly Ser
1               5                   10                  15

Ala Ala Ala Gly Gln Asp Leu Ile Ser Val Pro Arg Asn Thr Phe Met
            20                  25                  30

Thr Leu Leu Gln Thr Asn Leu Asp Asn Lys Pro Pro Arg Gln Thr Pro
        35                  40                  45

Leu Pro Tyr Ala Ala Pro Leu Pro Pro Phe Ser His Gln Ala Ile Ala
    50                  55                  60

Thr Ala Pro Ser Tyr Gly Pro Gly Ala Gly Ala Val Ala Pro Ala Gly
65                  70                  75                  80

Gly Tyr Phe Thr Ser Pro Gly Gly Tyr Tyr Ala Gly Pro Ala Gly Gly
                85                  90                  95

Asp Pro Gly Ala Phe Leu Ala Met Asp Ala His Thr Tyr His Pro His
            100                 105                 110

Pro His Pro Pro Ala Tyr Phe Gly Leu Pro Gly Leu Phe Gly Pro
        115                 120                 125
```

```
Pro Pro Pro Val Pro Tyr Tyr Gly Ser His Leu Arg Ala Asp Tyr
    130             135             140
Val Pro Ala Pro Ser Arg Ser Asn Lys Arg Lys Arg Asp Pro Glu Glu
145             150             155             160
Asp Glu Glu Gly Gly Gly Leu Phe Pro Gly Asp Ala Thr Leu Tyr
                165             170             175
Arg Lys Asp Ile Ala Gly Leu Ser Lys Ser Val Asn Glu Leu Gln His
            180             185             190
Thr Leu Gln Ala Leu Arg Arg Glu Thr Leu Ser Tyr Gly His Thr Gly
        195             200             205
Val Gly Tyr Cys Pro Gln Gln Gly Pro Cys Tyr Thr His Ser Gly Pro
    210             215             220
Tyr Gly Phe Gln Pro His Gln Ser Tyr Glu Val Pro Arg Tyr Val Pro
225             230             235             240
His Pro Pro Pro Pro Thr Ser His Gln Ala Ala Gln Ala Gln Pro
                245             250             255
Pro Pro Pro Gly Thr Gln Ala Pro Glu Ala His Cys Val Ala Glu Ser
            260             265             270
Thr Ile Pro Glu Ala Gly Ala Ala Gly Asn Ser Gly Pro Arg Glu Asp
        275             280             285
Thr Asn Pro Gln Gln Pro Thr Thr Glu Gly His His Arg Gly Lys Lys
    290             295             300
Leu Val Gln Ala Ser Ala Ser Gly Val Ala Gln Ser Lys Glu Pro Thr
305             310             315             320
Thr Pro Lys Ala Lys Ser Val Ser Ala His Leu Lys Ser Ile Phe Cys
                325             330             335
Glu Glu Leu Leu Asn Lys Arg Val Ala
                340             345

(2) INFORMATION FOR SEQ ID NO: 5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 5:

Ala Val Asp Thr Gly Ser Gly Gly Gly Gln Pro His Asp Thr Ala
            5               10              15
Pro Arg Gly Ala Arg Lys Lys Gln
        20

(2) INFORMATION FOR SEQ ID NO: 6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 6:
```

Ser Thr Ala Val Ala Gln Ser Ala Thr Pro Ser Val Ser Ser Ile
                5                  10                 15
Ser Ser Leu Arg Ala Ala Thr Ser Gly Ala Thr Ala Ala Ala
                20                  25

(2) INFORMATION FOR SEQ ID NO: 7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 7:

Gly Val Pro Arg Arg Gln Arg Ala Ile Asp Lys Arg Gln Arg Ala
                5                  10                 15

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 8:

Gly Gln Pro His Asp Thr Ala Pro Arg Gly Ala Arg Lys Lys Gln
                5                  10                 15

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 9:

Thr Ala Val Ala Gln Ser Ala Thr Pro Ser Val Ser
                5                  10

(2) INFORMATION FOR SEQ ID NO: 10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 10:

Pro Ser Val Ser Ser Ser Ile Ser Ser Leu Arg Ala (2) INFORMATION FOR SEQ ID NO: 11:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 11:

Ser Val Ser Ser Ser Ile Ser Ser Leu Arg Ala Ala (2) INFORMATION FOR SEQ ID NO: 12:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 12:

Ser Ser Ser Ile Ser Ser Leu Arg Ala Ala Thr Ser (2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 13:

Ser Ile Ser Ser Leu Arg Ala Ala Thr Ser Gly Ala (2) INFORMATION FOR SEQ ID NO: 14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 14:

Ile Ser Ser Leu Arg Ala Ala Thr Ser Gly Ala Thr (2) INFORMATION FOR SEQ ID NO:15:

```
    (i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 15:

Arg Ala Ala Thr Ser Gly Ala Thr Ala Ala Ala Ser
                5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 16:

Ala Ala Val Asp Thr Gly Ser Gly Gly Gly Gly Gln
                5                   10

(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 17:

Ala Val Asp Thr Gly Ser Gly Gly Gly Gly Gln Pro
                5                   10

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Epstein-Barr virus (xi) SEQUENCE DESCRIPTION: SEQ ID NO: 18:

Val Asp Thr Gly Ser Gly Gly Gly Gly Gln Pro His
                5                   10

(2) INFORMATION FOR SEQ ID NO:19:

(i) SEQUENCE CHARACTERISTICS:
        (A) LENGTH: 12 amino acids
        (B) TYPE: amino acid
```

-continued

```
            (C) STRANDEDNESS: single
            (D) TOPOLOGY: linear (ii) MOLECULE TYPE: peptide (vi) ORIGINAL SOURCE:
            (A) ORGANISM: Epstein-Barr virus (xi) SEQUENCE DESCRIPTION: SEQ ID NO: 19:

Asp Thr Gly Ser Gly Gly Gly Gln Pro His Asp
                5                   10

(2) INFORMATION FOR SEQ ID NO: 20:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Epstein-Barr virus (xi) SEQUENCE DESCRIPTION: SEQ ID NO: 20:

Gly Gly Gly Gln Pro His Asp Thr Ala Pro Arg Gly
                5                   10

(2) INFORMATION FOR SEQ ID NO: 21:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Epstein-Barr virus (xi) SEQUENCE DESCRIPTION: SEQ ID NO: 21:

Gly Gln Pro His Asp Thr Ala Pro Arg Gly Ala Arg
                5                   10

(2) INFORMATION FOR SEQ ID NO: 22:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Epstein-Barr virus (xi) SEQUENCE DESCRIPTION: SEQ ID NO: 22:

Gln Pro His Asp Thr Ala Pro Arg Gly Ala Arg Lys
                5                   10
```